United States Patent
Viswanathan et al.

(10) Patent No.: US 12,150,698 B2
(45) Date of Patent: Nov. 26, 2024

(54) SYSTEMS, APPARATUSES, AND METHODS FOR VENTRICULAR FOCAL ABLATION

(71) Applicant: Boston Scientific Scimed, Inc., Maple Grove, MN (US)

(72) Inventors: Raju Viswanathan, Mountain View, CA (US); Gary L. Long, Cincinnati, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 117 days.

(21) Appl. No.: 17/150,164

(22) Filed: Jan. 15, 2021

(65) Prior Publication Data

US 2021/0137592 A1    May 13, 2021

Related U.S. Application Data

(63) Continuation of application No. 16/817,410, filed on Mar. 12, 2020, now Pat. No. 10,893,905, which is a
(Continued)

(51) Int. Cl.
*A61B 18/14*     (2006.01)
*A61B 5/283*    (2021.01)
*A61B 18/00*    (2006.01)

(52) U.S. Cl.
CPC .......... *A61B 18/1492* (2013.01); *A61B 5/283* (2021.01); *A61B 2018/00077* (2013.01);
(Continued)

(58) Field of Classification Search
CPC ................ A61B 18/14; A61B 18/1492; A61B 2018/00077; A61B 2018/00083;
(Continued)

(56) References Cited

U.S. PATENT DOCUMENTS 4,200,104 A    4/1980 Harris
4,470,407 A    9/1984 Hussein
(Continued)

FOREIGN PATENT DOCUMENTS

EP    1042990 A1    10/2000
EP    1125549 A2    8/2001
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — Adam Z Minchella
(74) *Attorney, Agent, or Firm* — Nelson Mullins Riley & Scarborough LLP

(57) ABSTRACT

Systems, devices, and methods for electroporation ablation therapy are disclosed, with the system including a pulse waveform signal generator for medical ablation therapy, and an endocardial ablation device includes an inflatable member and at least one electrode for focal ablation pulse delivery to tissue. The signal generator may deliver voltage pulses to the ablation device in the form of a pulse waveform. The system may include a cardiac stimulator for generation of pacing signals and for sequenced delivery of pulse waveforms in synchrony with the pacing signal.

20 Claims, 26 Drawing Sheets

Related U.S. Application Data continuation of application No. PCT/US2018/050660, filed on Sep. 12, 2018.

(60) Provisional application No. 62/557,390, filed on Sep. 12, 2017.

(52) U.S. Cl.
CPC ............... *A61B 2018/00083* (2013.01); *A61B 2018/00232* (2013.01); *A61B 2018/00357* (2013.01); *A61B 2018/00577* (2013.01); *A61B 2018/00613* (2013.01); *A61B 2018/00767* (2013.01); *A61B 2018/1467* (2013.01)

(58) Field of Classification Search
CPC .. A61B 2018/0022; A61B 2018/00232; A61B 2018/00357; A61B 2018/00577; A61B 2018/00613; A61B 2018/00767; A61B 2018/1467; A61B 5/6853; A61B 2018/1266
See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Hassett et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,405,732 B1 | 6/2002 | Edwards et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |

(56) References Cited

U.S. PATENT DOCUMENTS

| | | |
|---|---|---|
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro'et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | De et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |

(56) References Cited

U.S. PATENT DOCUMENTS

| | | |
|---|---|---|
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Jean-Pierre |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,617,467 B2 | 4/2020 | Viswanathan et al. |
| 10,660,702 B2 | 5/2020 | Viswanathan et al. |
| 10,687,892 B2 | 6/2020 | Long et al. |
| 10,842,561 B2 | 11/2020 | Viswanathan et al. |
| 2001/0000791 A1 | 5/2001 | Suorsa et al. |
| 2001/0007070 A1 | 7/2001 | Stewart et al. |
| 2001/0020167 A1* | 9/2001 | Woloszko ............ A61B 18/149 606/49 |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0120304 A1* | 8/2002 | Mest ............ A61N 1/36114 607/14 |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0204185 A1 | 10/2003 | Sherman et al. |
| 2003/0229379 A1 | 12/2003 | Maynard |
| 2004/0002748 A1 | 1/2004 | Ryan et al. |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2005/0288730 A1* | 12/2005 | Deem ............ A61N 1/36103 514/356 |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1* | 6/2006 | Demarais ............ A61N 1/40 607/2 |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0083192 A1* | 4/2007 | Welch ............ A61B 18/1492 606/41 |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076498 A1 | 3/2009 | Saadat et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0171352 A1* | 7/2009 | Sutter ............ A61B 18/1402 606/49 |
| 2009/0182287 A1* | 7/2009 | Kassab ............ A61B 5/287 606/41 |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |

(56) References Cited

U.S. PATENT DOCUMENTS

| | | |
|---|---|---|
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0204560 A1* | 8/2010 | Salahieh ............. A61B 5/01 606/41 |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0301587 A1* | 12/2011 | Deem ............... A61B 18/1815 606/41 |
| 2011/0313417 A1 | 12/2011 | De et al. |
| 2012/0029512 A1 | 2/2012 | Willard et al. |
| 2012/0046570 A1 | 2/2012 | Mllegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0123778 A1* | 5/2013 | Richardson ........ A61B 18/1492 606/41 |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0257130 A1 | 9/2014 | Cao et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0330266 A1 | 11/2014 | Thompson et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |

(56) References Cited

U.S. PATENT DOCUMENTS

| | | |
|---|---|---|
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331254 A1 | 11/2016 | Tegg et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0112405 A1 | 4/2017 | Sterrett et al. |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1* | 1/2019 | Stewart ............ A61B 18/1492 |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |
| 2020/0046423 A1 | 2/2020 | Viswanathan et al. |
| 2020/0093539 A1 | 3/2020 | Long et al. |
| 2020/0289197 A1 | 9/2020 | Viswanathan et al. |

FOREIGN PATENT DOCUMENTS

| | | |
|---|---|---|
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |

(56) References Cited

FOREIGN PATENT DOCUMENTS

| | | |
|---|---|---|
| EP | 2934307 A1 | 10/2015 |
| EP | 3056242 A1 | 8/2016 |
| EP | 3111871 A1 | 1/2017 |
| EP | 3151773 B1 | 4/2018 |
| JP | 06-507797 A | 9/1994 |
| JP | 10-510745 A | 10/1998 |
| JP | 2000-508196 A | 7/2000 |
| JP | 2001-509415 A | 7/2001 |
| JP | 2005-516666 A | 6/2005 |
| JP | 2006-506184 A | 2/2006 |
| JP | 2007-325935 A | 12/2007 |
| JP | 2008-538997 A | 11/2008 |
| JP | 2009-500129 A | 1/2009 |
| JP | 2011-509158 A | 3/2011 |
| JP | 2012-050538 A | 3/2012 |
| JP | 2012-508083 A | 4/2012 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |
| WO | 97/25917 A1 | 7/1997 |
| WO | 97/37719 A1 | 10/1997 |
| WO | 99/02096 A1 | 1/1999 |
| WO | 99/04851 A1 | 2/1999 |
| WO | 99/22659 A1 | 5/1999 |
| WO | 99/49407 A1 | 9/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2011/028310 A1 | 3/2011 |
| WO | 2011/154805 A1 | 12/2011 |
| WO | 2012/051433 A2 | 4/2012 |
| WO | 2012/097067 A1 | 7/2012 |
| WO | 2012/153928 A2 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/066322 A1 | 5/2015 |
| WO | 2015/099786 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/070559 A1 | 4/2017 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/201504 A1 | 11/2017 |
| WO | 2017/218734 A1 | 12/2017 |
| WO | 2018/005511 A1 | 1/2018 |
| WO | 2018/106569 A1 | 6/2018 |
| WO | 2018/200800 A1 | 11/2018 |
| WO | 2019/023259 A2 | 1/2019 |
| WO | 2019/023280 A1 | 1/2019 |
| WO | 2019/035071 A1 | 2/2019 |
| WO | 2019/133606 A1 | 7/2019 |
| WO | 2019/133608 A1 | 7/2019 |
| WO | 2019/136218 A1 | 7/2019 |
| WO | 2019/181612 A1 | 9/2019 |
| WO | 2019/234133 A1 | 12/2019 |

OTHER PUBLICATIONS

Hobbs, E. P., "Investor Relations Update: Tissue Ablation via Irreversible Electroporation (IRE)," Powerpoint (2004), 16 pages.

Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].

Madhavan, M. et al., "Novel Percutaneous Epicardial Autonomic Modulation in the Canine for Atrial Fibrillation: Results of an Efficacy and Safety Study," Pace, 00:1-11 (2016).

Neven, K. et al., "Epicardial linear electroporation ablation and lesion size," Heart Rhythm, 11:1465-1470 (2014).

Neven, K. et al., "Myocardial Lesion Size After Epicardial Electroporation Catheter Ablation After Subxiphoid Puncture," Circ Arrhythm Electrophysiol., 7(4):728-733 (2014).

Neven, K. et al., "Safety and Feasibility of Closed Chest Epicardial Catheter Ablation Using Electroporation," Circ Arrhythm Electrophysiol., 7:913-919 (2014).

Van Driel, V.J.H.M. et al., "Low vulnerability of the right phrenic nerve to electroporation ablation," Heart Rhythm, 12:1838-1844 (2015).

Van Driel, V.J.H.M. et al., "Pulmonary Vein Stenosis After Catheter Ablation Electroporation Versus Radiofrequency," Circ Arrhythm Electrophysiol., 7(4):734-738 (2014).

Wittkampf, F.H. et al., "Feasibility of Electroporation for the Creation of Pulmonary Vein Ostial Lesions," J Cardiovasc Electrophysiol, 22(3):302-309 (Mar. 2011).

Wittkampf, F.H. et al., "Myocardial Lesion Depth With Circular Electroporation Ablation," Circ. Arrhythm Electrophysiol., 5(3):581-586 (2012).

\* cited by examiner

SYSTEMS, APPARATUSES, AND METHODS FOR VENTRICULAR FOCAL ABLATION

CROSS-REFERENCE TO RELATED APPLICATIONS

This application is a continuation of U.S. application Ser. No. 16/817,410, filed on Mar. 12, 2020, which is a continuation of International Patent Application No. PCT/US2018/050660, filed on Sep. 12, 2018, which claims priority to U.S. Provisional Application No. 62/557,390, filed on Sep. 12, 2017, the disclosures of each of which are hereby incorporated by reference in their entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally.

While pulsed DC voltages may drive electroporation under the right circumstances, there remains an unmet need for thin, flexible, atraumatic devices that effectively deliver high DC voltage electroporation ablation therapy selectively to endocardial tissue in regions of interest while minimizing damage to healthy tissue.

SUMMARY

Described here are systems, devices, and methods for ablating tissue through irreversible electroporation. Generally, an apparatus for delivering a pulse waveform to tissue may include a catheter shaft defining a longitudinal axis. An inflatable member may be coupled to a distal end of the catheter shaft. The inflatable member may have an outer surface including a set of electrically conductive portions. A first set of electrodes may be formed on a surface of the catheter shaft. A second set of electrodes may be formed distal to the first set of electrodes on the surface of the catheter shaft. The second set of electrodes may be electrically coupled to the outer surface of the inflatable member and electrically isolated from the first set of electrodes.

In some embodiments, an apparatus may include a catheter shaft defining a longitudinal axis. An inflatable member may be coupled to a distal end of the catheter shaft. A first set of electrodes may be formed on a surface of the catheter shaft. A second electrode may be formed on the inflatable member and electrically isolated from the first set of electrodes.

In some embodiments, an apparatus may include a catheter shaft defining a longitudinal axis. An inflatable member may be coupled to a distal end of the catheter shaft. A first set of electrodes may be formed on the inflatable member and disposed proximal to an equatorial plane of the inflatable member. A second set of electrodes may be formed on the inflatable member and disposed distal to the equatorial plane of the inflatable member. The second set of electrodes may be electrically isolated from the first set of electrodes.

In some embodiments, a system may include a signal generator configured for generating a pulse waveform. An ablation device may be coupled to the signal generator and configured for receiving the pulse waveform. The ablation device may be include a handle, a catheter shaft defining a longitudinal axis, and an inflatable member coupled to a distal end of the catheter shaft. The inflatable member may have an outer surface including a set of electrically conductive portions. A first set of electrodes may be formed on a surface of the catheter shaft. A second set of electrodes may be formed distal to the first set of electrodes on the surface of the catheter shaft. The second set of electrodes may be electrically coupled to the outer surface of the inflatable member and electrically isolated from the first set of electrodes.

In some embodiments, an apparatus may include a catheter shaft defining a longitudinal axis. An annular inflatable member may be coupled to a distal end of the catheter shaft. The inflatable member may define an annular inflatable member lumen therethrough. A first electrode may be disposed on a distal end of the annular inflatable member. The first electrode may have a substantially planar portion. A second electrode may extend from, and be distal to, the annular inflatable member lumen and be spaced apart from the first electrode.

In some embodiments, the first set of electrodes may have a polarity opposite to a polarity of the second set of electrodes during delivery of a pulse waveform. In some embodiments, the first set of electrodes may have a polarity opposite to the polarity of the second electrode during delivery of a pulse waveform. In some embodiments, the first set of electrodes may have a polarity opposite to the polarity of the second set of electrodes during delivery of the pulse waveform.

In some embodiments, the catheter shaft may include a deflectable portion formed between the first set of electrodes and the second set of electrodes. The deflectable portion may be configured for deflecting a portion of the catheter including the second set of electrodes and the inflatable member up to about 210 degrees relative to the longitudinal axis. In some embodiments, a fluid source may be coupled to the inflatable member and configured to inflate the inflatable member.

In some embodiments, one or more electrodes of the first set of electrodes and one or more electrodes of the second set of electrodes may have an insulated electrical lead associated therewith, the insulated electrical lead configured for sustaining a voltage potential of at least about 700 V without dielectric breakdown of its corresponding insulation, the insulated electrical lead disposed in a lumen of the catheter shaft. In some embodiments, one or more electrodes of the first set of electrodes and the second electrode may have an insulated electrical lead associated therewith, the insulated electrical lead configured for sustaining a voltage potential of at least about 700 V without dielectric breakdown of its corresponding insulation, the insulated electrical lead disposed in a lumen of the catheter shaft.

In some embodiments, one or more electrodes of the first set of electrodes and one or more electrodes of the second set of electrodes may be independently addressable. In some embodiments, one or more electrodes of the first set of electrodes and the second electrode may be independently addressable.

In some embodiments, a distal-most electrode of the first set of electrodes may be spaced apart from a proximal most electrode of the second set of electrodes by between about 2 mm and about 10 mm. In some embodiments, a distal-most electrode of the first set of electrodes may be spaced apart by at least about 5 mm from a proximal end of the inflatable member. In some embodiments, the first set of electrodes may be formed on a portion of the catheter shaft having a length of between about 1 mm and about 12 mm. In some embodiments, the inflatable member has a cross-sectional diameter in its equatorial plane of between about 5 mm and about 15 mm. In some embodiments, the inflatable member may have a length of up to about 22 mm. In some embodiments, each electrode of the first set of electrodes has a width of between about 1 mm and about 5 mm and wherein adjacent electrodes of the first set of electrodes are spaced apart by between about 1 mm and about 5 mm.

In some embodiments, the inflatable member may have an asymmetric shape in a proximal-to-distal direction. In some embodiments, the inflatable member may have a bulbous shape. In some embodiments, the inflatable member may have a polyhedral shape. In some embodiments, a biocompatible coating may be formed on an outer surface of the inflatable member. In some embodiments, the distal end of the catheter may extend into an inner volume of the inflatable member. In some embodiments, a set of splines may be coupled to the catheter and an inner surface of the inflatable member. The set of splines may be configured for translation along the longitudinal axis to transition between a first configuration where the set of splines are approximately parallel to the longitudinal axis and a second configuration where the set of splines bias away from the longitudinal axis.

In some embodiments, the pulse waveform may include a first level of a hierarchy of the pulse waveform in the form of a first set of pulses, each pulse having a pulse time duration, a first time interval separating successive pulses. A second level of the hierarchy of the pulse waveform includes a plurality of first sets of pulses as a second set of pulses, a second time interval separating successive first sets of pulses, the second time interval being at least three times the duration of the first time interval. A third level of the hierarchy of the pulse waveform includes a plurality of second sets of pulses as a third set of pulses, a third time interval separating successive second sets of pulses, the third time interval being at least thirty times the duration of the second level time interval. In some of these embodiments, the pulse waveform includes a fourth level of the hierarchy of the pulse waveform includes a plurality of third sets of pulses as a fourth set of pulses, a fourth time interval separating successive third sets of pulses, the fourth time interval being at least ten times the duration of the third level time interval.

In some embodiments, a distal portion of the catheter shaft further includes a radiopaque portion. In some embodiments, the catheter shaft defines a shaft lumen therethrough. In some embodiments, the first set of electrodes are formed on a distal portion of the catheter shaft.

In some embodiments, there are no electrodes formed on the outer surface of the inflatable member. In some embodiments, a conductive element may be formed on a surface of the inflatable member. In some embodiments, the conductive element may include a set of spaced apart conductive stripes extending between ends of the inflatable member. In some embodiments, the conductive element may be electrically connected to the second set of electrodes. In some embodiments, each stripe of the set of stripes may intersect at one or more of a proximal end and a distal end of the inflatable member.

In some embodiments, the conductive element may include an interlaced structure defining a set of apertures. In some embodiments, a first conductive element may be disposed on an outer surface of the inflatable member and a second conductive element may be disposed on an inner surface of the inflatable member. The first conductive element may have an opposite polarity to the second conductive element during delivery of a pulse waveform.

In some embodiments, a first conductive element may be disposed on an outer surface of the inflatable member and a second conductive element may be disposed on an inner surface of the inflatable member. The first conductive element may have an opposite polarity to the second conductive element during delivery of the pulse waveform.

In some embodiments, the first set of electrodes may be disposed on an outer surface of the catheter shaft and one or more electrodes of the second set of electrodes may be disposed on an inner surface of the catheter shaft. In some embodiments, the second electrode may be configured to receive electrophysiology data. In some embodiments, the second electrode may be a distal electrode. In some embodiments, the second electrode may be the only electrode formed on the outer surface of the inflatable member.

In some embodiments, a distal end of the inflatable member may have a concave surface facing away from a proximal end of the inflatable member. In some embodiments, the inflatable member may have a set of curved faces. In some embodiments, at least one electrode of the second set of electrodes is formed on one face of the inflatable member. In some embodiments, one or more electrodes of the second set of electrodes may be concave.

In some embodiments, the inflatable member may have a set of curved edges. In some embodiments, each electrode of the second set of electrodes may have a diameter of between about 3 mm and about 15 mm. In some embodiments, a distal-most electrode of the first set of electrodes may be spaced apart from a proximal end of the inflatable member by at least about 3 mm. In some embodiments, the inflatable member when inflated may have a cross-sectional diameter at its largest portion of between about 6 mm and about 22 mm.

In some embodiments, the annular inflatable member when inflated may have a diameter of between about 10 mm and about 15 mm. In some embodiments, the second electrode may have a length of between about 2 mm and about 10 mm. In some embodiments, the annular inflatable member lumen may have a diameter of between about 4 mm and about 15 mm.

In some embodiments, a second set of electrodes may be formed on the inflatable member between the first set of electrodes and the second electrode. In some embodiments, the second electrode may be independently addressable. In some embodiments, each electrode of the second set of electrodes may be independently addressable.

In some embodiments, the second set of electrodes may be formed on the inflatable member on an approximate plane approximately perpendicular to the longitudinal axis. In some embodiments, each electrode of the second set of electrodes may have a circular or elliptical shape. In some embodiments, a major axis of each electrode of the second set of electrodes having the elliptical shape may be substantially parallel to the longitudinal axis.

In some embodiments, the second set of electrodes may include a distal electrode formed at a distal end of the inflatable member. In some embodiments, each electrode of the second set of electrodes may have a circular or elliptical shape. In some embodiments, a major axis of each electrode of the second set of electrodes having the elliptical shape except the distal electrode is substantially parallel to the longitudinal axis.

In some embodiments, a method of focal ablation via irreversible electroporation includes the steps of advancing an ablation device towards an endocardial wall. The ablation device may include a catheter shaft defining a longitudinal axis and an inflatable member coupled to a distal end of the catheter shaft. The inflatable member may have an outer surface including a set of electrically conductive portions. A first set of electrodes may be formed on a surface of the catheter shaft. A second set of electrodes may be formed distal to the first set of electrodes on the surface of the catheter shaft. The second set of electrodes electrically may be coupled to the outer surface of the inflatable member and electrically isolated from the first set of electrodes. A pulse waveform may be generated. The pulse waveform may be delivered to the endocardial wall via the ablation device.

In some embodiments, one of the first set of electrodes and the second set of electrodes may be configured as anodes. The other of the first set of electrodes and the second set of electrodes may be configured as cathodes. In some embodiments, the inflatable member of the ablation device may be transitioned from a first configuration to a second configuration. In some embodiments, transitioning the inflatable member from the first configuration to the second configuration includes infusing the inflatable member with saline. In some embodiments, pulsed electric field ablation energy may be delivered through the first set of electrodes and the second set of electrodes of the ablation device. In some embodiments, the ablation device is configured to generate an electric field intensity of between about 200 V/cm and about 800 V/cm.

In some embodiments, the ablation device may include a handle. The method may further include the steps of deflecting a portion of the ablation device using the handle. In some embodiments, first electrophysiology data of the endocardial wall may be recorded. Second electrophysiology data of the endocardial wall may be recorded after delivering the pulse waveform. In some embodiments, the first electrophysiology data and the second electrophysiology data may include intracardiac ECG signal data of the endocardial wall. In some embodiments, a diagnostic catheter may be advanced into the endocardial wall and recording the first electrophysiology data and the second electrophysiology data using the diagnostic catheter. In some embodiments, the first electrophysiology data and the second electrophysiology data may be recorded using the ablation device in the second configuration.

In some embodiments, the method may include the steps of creating a transseptal opening into a left atrium, advancing a guidewire and a sheath into the left atrium through the transseptal opening, and advancing the ablation device into a ventricle over the guidewire. In some embodiments, the method may include the steps of creating a first access site in a patient, advancing the guidewire through the first access site and into a right atrium, advancing the dilator and a sheath over the guidewire and into the right atrium, advancing the dilator from the right atrium into the left atrium through an interatrial septum to create the transseptal opening, and dilating the transseptal opening using the dilator. In some embodiments, a second access site may be created in the patient for advancing a cardiac stimulator. In some embodiments, the method may include the steps of advancing the cardiac stimulator into a right ventricle, generating a pacing signal for cardiac stimulation of the heart using the cardiac stimulator, and applying the pacing signal to the heart using the cardiac stimulator, the pulse waveform generated in synchronization with the pacing signal.

In some embodiments, the method may include the step of fluoroscopically imaging a radiopaque portion of the ablation device during one or more steps. In some embodiments, the first access site is a femoral vein. In some embodiments, the interatrial septum includes a fossa ovalis. In some embodiments, the endocardial wall is a ventricle.

In some embodiments, the pulse waveform may include a first level of a hierarchy of the pulse waveform in the form of a first set of pulses, each pulse having a pulse time duration, a first time interval separating successive pulses. A second level of the hierarchy of the pulse waveform includes a plurality of first sets of pulses as a second set of pulses, a second time interval separating successive first sets of pulses, the second time interval being at least three times the duration of the first time interval. A third level of the hierarchy of the pulse waveform includes a plurality of second sets of pulses as a third set of pulses, a third time interval separating successive second sets of pulses, the third time interval being at least thirty times the duration of the second level time interval. In some of these embodiments, the pulse waveform includes a fourth level of the hierarchy of the pulse waveform includes a plurality of third sets of pulses as a fourth set of pulses, a fourth time interval separating successive third sets of pulses, the fourth time interval being at least ten times the duration of the third level time interval.

BRIEF DESCRIPTION OF THE DRAWINGS

FIG. 2A is a side view of an uninflated ablation device. FIG. 2B is a side view of an inflated ablation device. FIG. 2C is a side view of another embodiment of an inflated ablation device. FIG. 2D is a side view of another embodiment of an inflated ablation device.

FIGS. 5A-5J are side and perspective views of ablation devices, according to other embodiments. FIG. 5A is a side view of an ablation device. FIG. 5B is a cross-sectional side view of the ablation device depicted in FIG. 5A. FIG. 5C is a cross-sectional side view of another embodiment of an ablation device. FIG. 5D is a perspective view of the ablation device depicted in FIG. 5C. FIG. 5E is a cross-sectional side view of the ablation device depicted in FIG. 5C. FIG. 5F is a perspective view of another embodiment of an ablation device. FIG. 5G is a perspective view of the ablation device depicted in FIG. 5F. FIG. 5H is a perspective view of the ablation device depicted in FIG. 5F. FIG. 5I is a perspective view of another embodiment of an ablation device. FIG. 5J is a cross-sectional side view of the ablation device depicted in FIG. 5I.

DETAILED DESCRIPTION

Figure 1:
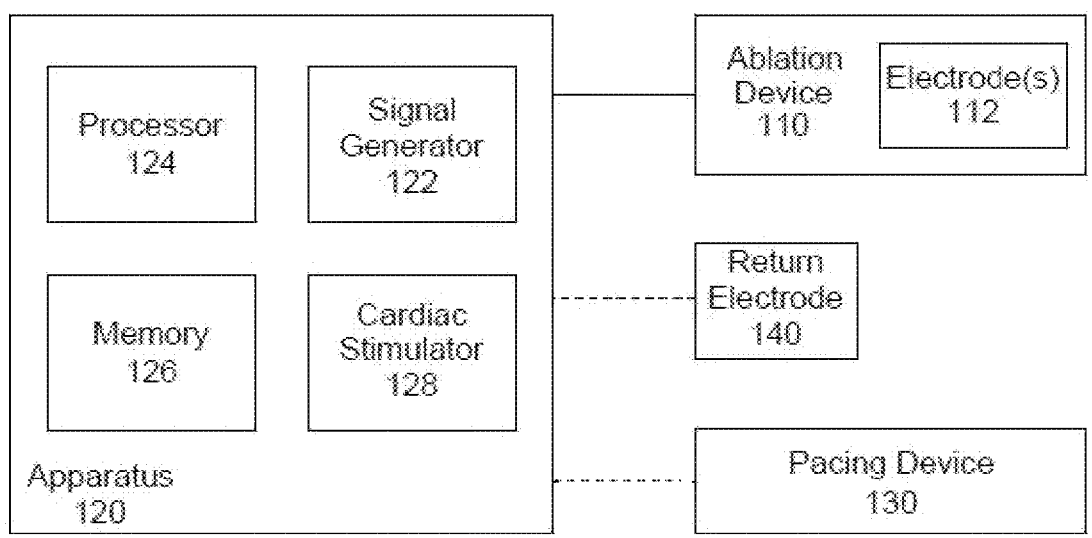
FIG. 1 is a block diagram of an electroporation system, according to embodiments.

Described here are systems, devices, and methods for ablating tissue through irreversible electroporation. Generally, a system for delivering a pulse waveform to tissue may include a signal generator configured for generating a pulse waveform and an ablation device coupled to the signal generator and configured to receive the pulse waveform. The ablation device may include a conductive inflatable member (e.g., balloon) coupled to a distal end of a catheter shaft for delivering energy to ablate tissue by irreversible electroporation. A conductive metal pattern may be disposed on an outer surface of the inflatable member. One or more electrodes may be formed proximal to the inflatable member on a surface of the catheter shaft. In some embodiments, the ablation device may be configured for delivering the pulse waveform to tissue during use via one or more of the electrodes and inflatable member that forms a bipole. In some embodiments, capacitive voltage delivery may be provided using biphasic waveforms across a thickness of the inflatable member wall. Embodiments of the ablation device described herein may deliver energy to tissue sufficient for irreversible electroporation through the inflatable member of the ablation device that functions as an electrode. The inflatable member is inflatable so as to allow an electric field and corresponding focal ablation lesions to be generated. In some embodiments, the ablation device may form focal ablation lesions at a depth of between about 2 mm to about 15 mm or more that may be suitable to form wide and deep ablations in a ventricular wall.

In some embodiments, the ablation devices described herein may be useful in treating ventricular arrhythmias (e.g., re-entrant ventricular tachycardia) that may occur in the ventricle and cause arrhythmia due to the cardiac depolarization signal not completing a normal circuit, but rather, an alternative circuit such as looping back upon itself (e.g., re-entrant circuit). For example, the ablation devices described herein may be used for scar homogenization or "debulking" that may ablate one or more portions of scar tissue in order to electrically isolate and/or destroy re-entrant circuits. The systems, devices, and methods described herein may be used to create one or more focal ablation lesions using an endocardial approach, and in other embodiments, may be used in an epicardial approach.

In some embodiments, the ablation device may include one or more electrodes configured to receive ECG signals and used to generate an anatomical map of the patient. For example, an ECG recording electrode may be disposed on one or more of the inflatable member and catheter shaft. This may allow the ablation device to both map and ablate tissue, thereby reducing cost, complexity, and procedure time when a separate mapping catheter is not used.

The systems, devices, and methods described herein may be used to generate large electric field magnitudes at desired regions of interest to generate irreversible electroporation. An irreversible electroporation system as described herein may include a signal generator and a processor configured to apply one or more voltage pulse waveforms to a selected set of electrodes and an inflatable member of an ablation device to deliver energy to a region of interest (e.g., ablation energy for a set of tissue in a ventricle). The pulse waveforms disclosed herein may aid in therapeutic treatment of a variety of cardiac arrhythmias (e.g., atrial fibrillation, re-entry ventricular arrhythmia, ventricular tachycardia, and/or the like). In order to deliver the pulse waveforms generated by the signal generator, one or more electrodes of the ablation device may have an insulated electrical lead configured for sustaining a voltage potential of at least about 700 V without dielectric breakdown of its corresponding insulation. In some embodiments, at least some of the electrodes may be independently addressable such that each electrode may be controlled (e.g., deliver energy) independently of any other electrode of the device. In this manner, the electrodes may deliver different energy waveforms with different timing synergistically for electroporation of tissue.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYS- TEMS, APPARATUSES AND METHODS FOR DELIVERY OF ABLATIVE ENERGY TO TISSUE," the contents of which are hereby incorporated by reference in its entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, an ablation device may include one or more catheters, guidewires, inflatable members, and electrodes. The ablation device may transform into different configurations (e.g., deflated and inflated) to position the device within an endocardial space.

Generally, to ablate tissue, one or more catheters may be advanced in a minimally invasive fashion through vasculature to a target location. The methods described here may include introducing a device into an endocardial space of the heart and disposing the device in contact with a ventricle or other cardiac surface. A pulse waveform may be generated and delivered to one or more electrodes and a conductive inflatable member of the device to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes and an inflatable member (e.g., balloon) for the selective and rapid application of DC voltage to drive electroporation. As described herein, the systems and devices may be deployed endocardially to treat cardiac arrhythmias. Voltage pulse waveforms may be applied to a subset of the electrodes, with suitable anode/cathode electrode selections. A pacing signal for cardiac stimulation may be generated and used to generate the pulse waveform by the signal generator in synchronization with the pacing signal.

Generally, the systems and devices described herein include one or more catheters configured to ablate tissue in a ventricle of a heart. FIG. 1 illustrates an ablation system (100) configured to deliver voltage pulse waveforms. The system (100) may include an apparatus (120) including a signal generator (122), processor (124), memory (126), and cardiac stimulator (128). The apparatus (120) may be coupled to an ablation device (110), and optionally to a pacing device (130).

The signal generator (122) may be configured to generate pulse waveforms for irreversible electroporation of tissue, such as, for example, ventricular tissue, such as that of the left ventricle. For example, the signal generator (122) may be a voltage pulse waveform generator and be configured to deliver a pulse waveform to the ablation device (110). The return electrode (140) in some embodiments may be coupled to a patient (e.g., disposed on a patient's back) to allow current to pass from the ablation device (110) through the patient and then to the return electrode (140). In other embodiments, the return electrode (140) may be part of the ablation device so that the electrode bipole is on the device. The processor (124) may incorporate data received from memory (126), cardiac stimulator (128), and pacing device (130) to determine the parameters (e.g., amplitude, width, duty cycle, etc.) of the pulse waveform to be generated by the signal generator (122). The memory (126) may further store instructions to cause the signal generator (122) to execute modules, processes and/or functions associated with the system (100), such as pulse waveform generation and/or cardiac pacing synchronization. For example, the memory (126) may be configured to store pulse waveform and/or heart pacing data for pulse waveform generation and/or cardiac pacing, respectively.

In some embodiments, the ablation device (110) may include a catheter having an inflatable member (e.g., balloon) configured to deliver the pulse waveforms described in more detail below. In each of the embodiments described herein, the inflatable member may be inflated using gas, liquid, combinations thereof, and the like. For example, the ablation device (110) may be introduced into an endocardial space and positioned to align the inflatable member to a tissue surface, and then deliver the pulse waveforms to ablate tissue. The ablation device (110) may include one or more electrodes (112), which may, in some embodiments, be independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 3,000 V across its thickness without dielectric breakdown. For example, the electrodes (112) may be grouped into one or more anode-cathode subsets such as, for example, a subset including one proximal electrode and one distal electrode. In some embodiments, the distal electrode may include at least a portion of an inflatable member. As used herein, proximal is towards a handle of an ablation device and distal is towards a tip end of the ablation device.

When used, the pacing device (130) may be suitably coupled to the patient (not shown) and configured to receive a heart pacing signal generated by the cardiac stimulator (128) of the apparatus (120) for cardiac stimulation. An indication of the pacing signal may be transmitted by the cardiac stimulator (128) to the signal generator (122). Based on the pacing signal, an indication of a voltage pulse waveform may be selected, computed, and/or otherwise identified by the processor (124) and generated by the signal generator (122). In some embodiments, the signal generator (122) may be configured to generate the pulse waveform in synchronization with the indication of the pacing signal (e.g., within a common refractory window). For example, in some embodiments, the common refractory window may start substantially immediately following a ventricular pacing signal (or after a very small delay) and last for a duration of approximately 250 ms or less thereafter. In such embodiments, an entire pulse waveform may be delivered within this duration.

The processor (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Ablation Device

Figure 2A:
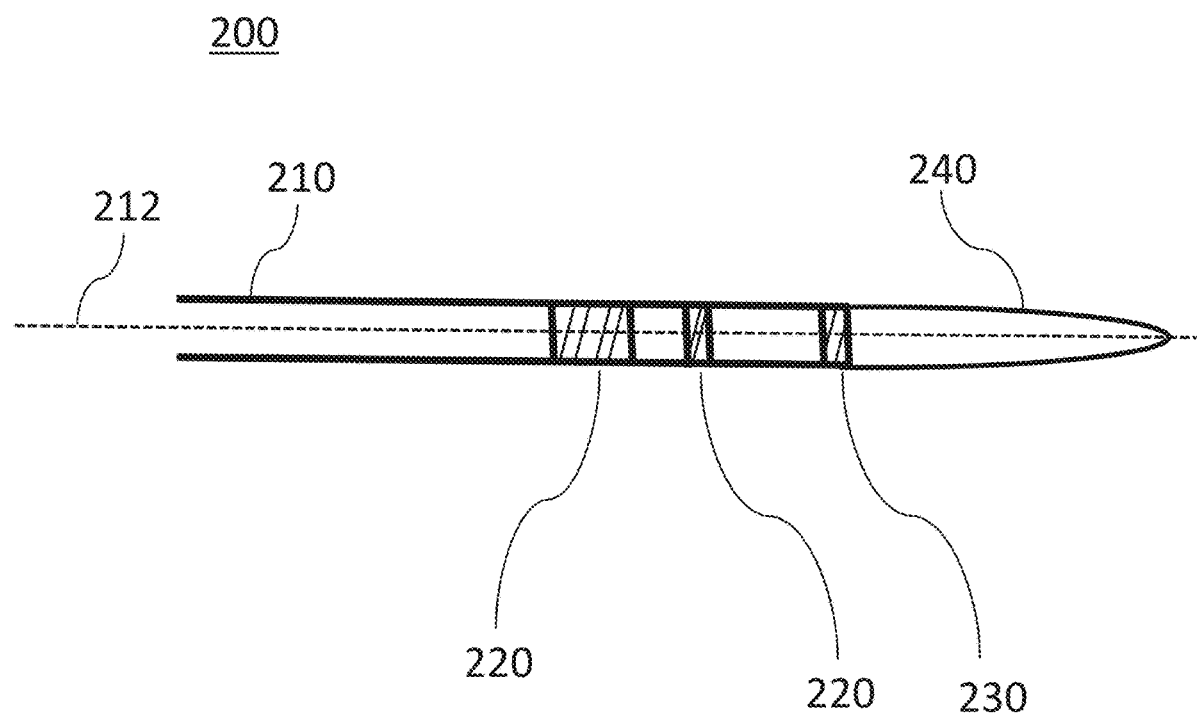
FIGS. 2A-2D are side views of an ablation device in various configurations, according to embodiments.

The systems described here may include one or more multi-electrode ablation devices configured to ablate tissue in a ventricle of a heart for treating indications such as ventricular arrhythmia. FIG. 2A is a side view of an ablation device (200) (e.g., structurally and/or functionally similar to the ablation device (110)) including a catheter shaft (210) and an inflatable member (e.g., balloon) (240) coupled to a distal end of the catheter shaft (210). In some embodiments, the ablation device (200) is useful for forming lesions on endocardial surfaces via focal ablation, such as an inner surface of a ventricle, as described herein. A distal portion of the inflatable member (240) may include and/or be formed in an atraumatic shape that reduces trauma to tissue (e.g., prevents and/or reduces the possibility of tissue puncture). The catheter shaft (210) and inflatable member (240) may be sized for advancement into an endocardial space (e.g., a left ventricle). The catheter shaft (210) may be flexible so as to be deflectable, as shown and discussed in more detail with respect to FIG. 3. Any of the catheter shafts described herein may include a shaft lumen therethrough. A set of electrical leads and/or a fluid (e.g., saline) may be disposed within the shaft lumen. The inflatable member (240) may be configured to transition between a first configuration (e.g., a deflated state) and a second configuration (e.g., an inflated state). In the first configuration, the inflatable member (240) may have a diameter that is about the same as a diameter of the catheter shaft (210) to aid in advancing the ablation device (200) through vasculature. For example, the inflatable member (240) in the first configuration may be approximately parallel to a longitudinal axis (212) of the catheter shaft (210). For example, the inflatable member (240) may be in a compressed or crimped configuration. In the second configuration, the inflatable member (240) may have a cross-sectional diameter at its largest portion (e.g., at its equatorial plane) in the range of between approximately 5 mm and approximately 15 mm. For example, the inflatable member (240) when inflated may bias away from the longitudinal axis. The inflatable member (240), or a portion thereof, may include a conductive outer surface (e.g., FIG. 2C) that may be configured as an anode or cathode for delivery of pulse waveform to tissue.

As shown in FIGS. 2A-2D, one or more electrodes (220, 230) may include a series of metallic bands or rings disposed along a surface of a catheter shaft (210). For example, the ablation device (200) may comprise a first set of electrodes (220) (e.g., one or more proximal electrodes) formed on a surface of a distal portion of the catheter shaft (210). In some embodiments, one or more electrodes (220, 230) may be formed on the catheter shaft (210) along its entire circumference. In some embodiments, one or more electrodes (220, 230) may be formed on the surface of a portion of a circumference of the catheter shaft (210). For example, electrode (220) may encircle the circumference of the catheter shaft (210). In some embodiments, one or more electrodes may be fully covered by a thin layer of dielectric coating for biphasic operation.

Figure 2B:
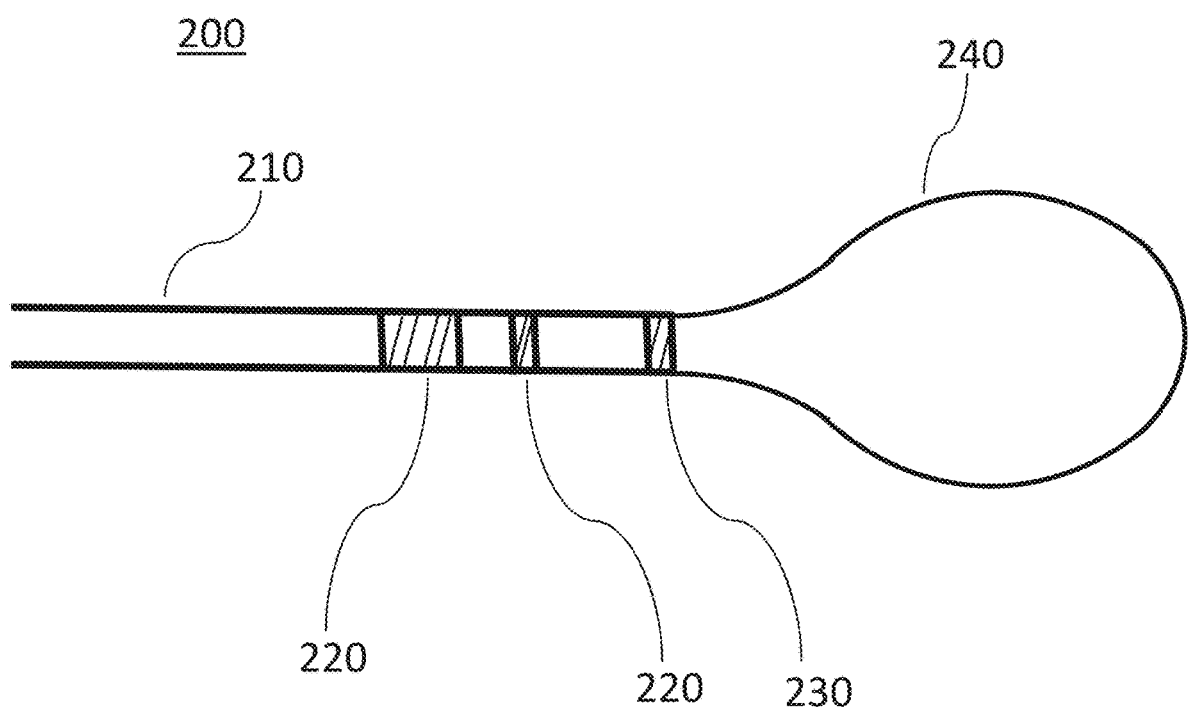

In FIGS. 2A-2B, there are no electrodes formed on the outer surface of the inflatable member (240). In some embodiments, the ablation device (200) may comprise a second set of electrodes (230) (e.g., a single distal electrode). The second set of electrodes (230) may be formed distal to the first set of electrodes (210) on the surface of the distal portion of the catheter shaft (210). In some embodiments, the electrodes (220, 230) may be shaped to conform to the shape of the catheter shaft (210). For example, the electrodes may be press fit (e.g., crimped) to the catheter shaft (210) or attached using a conductive adhesive. The catheter shaft (210) may include flexible portions (e.g., may be deflectable) between the electrodes (220, 230) to enhance flexibility and allow the device (200) to be deflected and aid in advancement through vasculature. In other embodiments, one or more electrodes (220, 230) may include a helical winding to enhance flexibility.

Each of the electrodes of any of the ablation devices discussed herein may be connected to an insulated electrical lead (not shown) leading to a handle (not shown) coupled to a proximal portion of the catheter. The insulation on each of the electrical leads may sustain an electrical potential difference of at least 700 V across its thickness without dielectric breakdown. In other embodiments, the insulation on each of the electrical leads may sustain an electrical potential difference of between about 200 V to about 3,000 V across its thickness without dielectric breakdown, including all values and sub-ranges in between. This allows the electrodes and inflatable member coupled thereto to effectively deliver electrical energy and to ablate tissue through irreversible electroporation. The electrodes (220, 230) may, for example, receive pulse waveforms generated by a signal generator (122) as discussed above with respect to FIG. 1.

The first set of electrodes (220) may be electrically coupled together using one or more electrical leads. The second set of electrodes (230) may be electrically coupled together using a different set of electrical leads. An outer surface of the inflatable member (240) may include a set of electrically conductive portions and coupled to the second set of electrodes (230) and electrically isolated from the first set of electrodes (220). In some embodiments, the first set of electrodes (220) may be configured as an anode while the second set of electrodes (230) and inflatable member (240) may be configured as a cathode. Accordingly, a bipole may be formed between the first set of electrodes (220) and the inflatable member (240) that results in an electric field capable of ablating tissue (e.g., myocardial cells on an inner surface or within a ventricle). The inflatable member (240) and the first set of electrodes (220) may be electrically isolated from each other. For example, the second set of electrodes (230) and the first set of electrodes (220) may each couple to a respective insulated electrical lead, with each lead having sufficient electrical insulation to sustain an electrical potential difference of at least 700 V across its thickness without dielectric breakdown. In some embodiments, the first set of electrodes (220) may have an opposite polarity to the second set of electrodes (230) during delivery of a voltage pulse waveform.

The first and second sets of electrodes (220, 230) may include an atraumatic shape to reduce trauma to tissue. For example, the electrodes (220, 230) may have an atraumatic shape including a rounded, flat, curved, and/or blunted portion. For example, the electrodes (220, 230) in FIGS. 2A-2D may be ring electrodes. In some embodiments, the first set of electrodes (220) may be located along any portion of the catheter shaft (210) proximal to the second set of electrodes (230). The second set of electrodes (230) may be disposed on a surface of the catheter shaft (240) and/or flush with the surface of the inflatable member (240) so as to be electrically coupled to the inflatable member (240). The electrodes (220, 230) may have the same or different sizes, shapes, and/or location along the catheter shaft (210). The spacing between electrodes of the first set of electrodes (220) may be configured to allow a distal portion of the catheter shaft (210) (e.g., deflectable portion) to deflect a predetermined amount (e.g., up to about 210 degrees of deflection). For example, the deflectable portion may be configured for deflecting a portion of the catheter including the second set of electrodes (230) and the inflatable member (240) up to about 210 degrees relative to the longitudinal axis.

In some embodiments, the first set of electrodes (220) may include electrodes disposed along a portion of the catheter shaft (210) having a length between about 1 mm and about 12 mm from a proximal end to a distal end of the first set of electrodes (220). The first set of electrodes (220) may be spaced apart from each other and wired together via one or more insulated leads so as to function as a single electrode (e.g., anode or cathode) while allowing the catheter shaft (210) to remain flexible and facilitate deflection. In some embodiments, the first set of electrodes (220) may be spaced apart from the second set of electrodes (230) by a length of between about 2 mm and about 10 mm.

For each of the ablation devices discussed herein, the electrodes (220, 230) may include biocompatible metals such as titanium, palladium, gold, silver, platinum or a platinum alloy. For example, the electrode may preferably include platinum or a platinum alloy. In some embodiments, the proximal electrodes may have a biocompatible coating that permits capacitive voltage delivery with biphasic waveforms. Each electrode (220, 230) may include an electrical lead having sufficient electrical insulation to sustain an electrical potential difference of at least 700 V across its thickness without dielectric breakdown. In other embodiments, the insulation on each of the electrical leads may sustain an electrical potential difference of between about 200 V to about 3,000 V across its thickness without dielectric breakdown, including all values and sub-ranges in between. The insulated electrical leads may run to the proximal handle portion of the ablation device (200) from where they may be connected to a suitable electrical connector. The catheter shaft (210) may be made of a flexible polymeric material such as Teflon, Nylon, Pebax, etc.

In some embodiments, one or more of the electrodes of the first and second sets of electrodes (220, 230) may be configured for receiving or sensing an ECG signal for recording electrophysiology data. Electrophysiology data may be used to generate an anatomical map that may be used to compare electrophysiology data recorded after energy delivery. The electrophysiology data may include intracardiac ECG signal data. The ablation device (200) may include one or more ECG signal electrodes. For example, one or more electrodes of the first set of electrodes (220) may be configured to receive an ECG signal. In some embodiments, an ECG signal electrode may be disposed on a surface of a distal end of an inflatable member (240) (not shown). The ECG signal electrode may be coupled to its own insulated electrical lead. The ECG signal electrode may be electrically isolated from the inflatable member (240) using, for example, a ring of insulation around the ECG signal electrode electrically isolating the ECG signal electrode from the conductive inflatable member. In these embodiments, the ablation device may be used to record electrophysiology data in place of a mapping catheter before and/or after tissue ablation. In some embodiments, the ablation device (200) may include a location sensor that may generate location data of the ablation device disposed within vasculature. The electrophysiology data and location data may be used to generate an anatomical map of the electrophysiology data. In some embodiments, the location sensor may include an electromagnetic coil disposed at a distal end of the inflatable member (240). In other embodiments, the location sensor may be disposed within a lumen of the catheter shaft (210).

In some embodiments, the inflatable member (240) may be coupled to the second set of electrodes (230), and configured to deliver a pulse waveform from a signal generator to tissue during use. The inflatable member (240) may be coupled to a distal portion of the catheter shaft (210) and configured to be conductive so as to function as one half of an anode-cathode pair for delivery of irreversible electroporation energy to tissue. The inflatable member (240) may be configured to transition between a first configuration (e.g., deflated inflatable member in FIG. 2A) and a second configuration (e.g., inflated inflatable member in FIGS. 2B-2D). The inflatable member (240) in the first configuration may be in a compact, deflated state suitable for advancement through vasculature. For example, the inflatable member (240) in the first configuration may be substantially empty of fluid, such as saline. The inflatable member (240) in the second configuration may hold a predetermined volume of saline that fills and inflates the inflatable member (240) to a predetermined size and shape (e.g., having a diameter to contact a diameter of a ventricle). The inflatable member (240) may transition to an intermediate configuration between the first and second configuration as necessary, for example, to conform to a lumen or advance the device through vasculature.

In some embodiments, the inflatable members as described herein may have an expandable structure and may be composed of materials including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS), and the like. The inflatable member may be embedded with other materials including, but not limited to metals, insulation, Kevlar, nylon fibers, and the like.

The distal portion of the inflatable member (240) disposed in a lumen (e.g., ventricle) may serve as a backstop to advancement of a distal portion of the catheter (200). By modifying a size of the inflatable member (240) and manipulating the deflection of the catheter shaft (210), the inflatable member (240) may be positioned at a target tissue site, such as, for example, near or in contact with the wall of a left ventricle. The distal portion of the catheter shaft (210) may include a set of electrodes (220, 230) (e.g., structurally and/or functionally similar to the electrode(s) (112)) where the inflatable member (240) may be configured to contact an inner radial surface of a tissue lumen (e.g., ventricle). In some embodiments, a cross-sectional diameter of the inflatable member (240) at is largest portion (e.g., equatorial plane) when inflated may be between about 5 mm and about 15 mm. A length of the inflatable member (240) when inflated may be up to about 22 mm. In some embodiments, the length of the inflatable member (240) may be substantially the same between the first and second configurations.

A proximal end of the inflatable member (240) may be coupled to a suitable electrical lead (e.g., via a second set of electrodes (230)) and connected to the signal generator (122) of FIG. 1. The inflatable member (240) may be configured as a cathode and the first set of electrodes (220) may be configured as an anode, or vice versa. In some embodiments, as described in detail herein, a set of proximal electrodes (220) and the inflatable member (240) may form a bipole. In this manner, the inflatable member (240) in the second configuration may be placed against, for example, an inner wall of the left ventricle in order to directly generate localized or focal lesions thereupon by activation of the first and second set of electrodes (220, 230) using any suitable combination of polarities. For example, the first and second set of electrodes (230, 240) may be configured with opposite polarities. In some embodiments, the ablation device may be configured to generate an electric field having an intensity of at least about 200 V/cm.

One or more of a biphasic signal may be applied to the bipole such that tissue may be ablated between the inflatable member (240) and the first set of electrodes (220) at a desired location in the ventricle. For example, a biphasic pulse waveform may be delivered between the sets of electrodes of opposed polarities, resulting in a zone of irreversible electroporation ablation in the region around the inflatable member.

In some embodiments, the inflatable member (240) when inflated may be configured to contact endocardial tissue while the second set of electrodes (220) (also sometimes referred to as "proximal electrodes") in the second configuration may not contact endocardial tissue. The electric field generated by the ablation device (200) due to conduction between the inflatable member (240) and proximal electrodes (220) through the blood pool and through tissue may result in focal ablation of tissue via irreversible electroporation.

In general, the inflatable member (240) when inflated may have an asymmetric shape in a proximal-to-distal direction, so that one end (for example the distal end) of the inflatable member (240) is more bulbous than the other end (for example the proximal end) of the inflatable member (240). The inflatable member (240) when inflated may be rotationally symmetric about the longitudinal axis of the catheter shaft (210). Such a bulbous distal portion can aid in positioning the device (200) in a ventricle as well as further controlling a size and depth of focal ablation. In this manner, the inflatable member (240) when inflated may be placed against, for example, an endocardial surface such as the inner surface of a ventricle in order to directly generate lesions thereupon by activation of appropriate electrodes (220, 230) using any suitable combination of polarities. For example, the inflatable member (240) may be placed at an endocardial surface and used to form a lesion via focal ablation (e.g., a spot lesion).

In some embodiments, an outer surface of the inflatable member (240) may include a set of conductive (e.g., metallized) portions. In this configuration, a bipole may be formed between the outer surface of the inflatable member (240) and the first set of electrodes (220) (e.g., proximal electrodes). For example, the outer surface of the inflatable member (240) may include a deposition of a biocompatible metal material (e.g., gold, silver, platinum), metal plating, printed metal nanoparticle ink, and/or the like. A portion of the inflatable member may include metal foil. The density of the metal material disposed on the outer surface of the inflatable member (240) may be such as to ensure electrical coupling with the second set of electrodes (230) (e.g., a distal ring electrode). The second set of electrodes (230) may be electrically coupled to a set of electrically conductive portions of the outer surface of the inflatable member (240) such that the inflatable member (240) is electrically coupled to a respective electrical lead. The electrode leads may be configured with sufficient insulation and high dielectric strength to be suitable for delivery of irreversible electroporation energy as described herein.

Figure 2C:
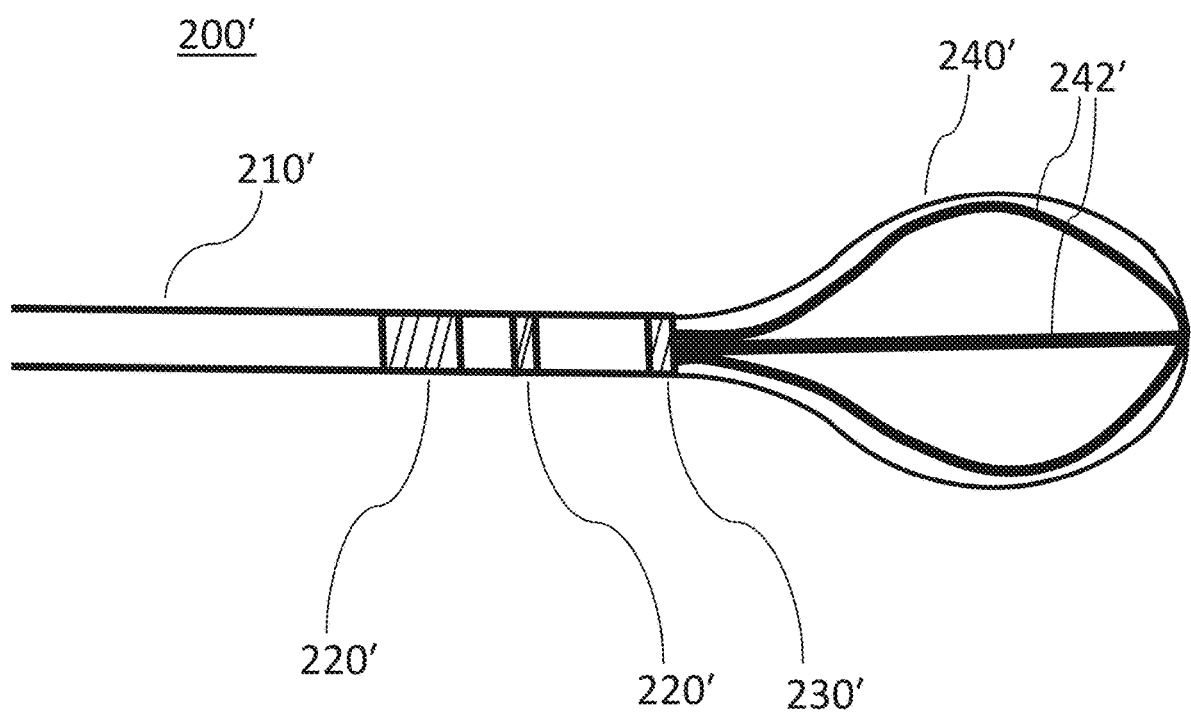

As shown in FIG. 2C, an ablation device (200') may include a catheter shaft (210') coupled at a distal end to an inflatable member (e.g., balloon) (240'). A first set of electrodes (220') and a second set of electrodes (230') may be disposed on a surface of the catheter shaft (210') and/or flush with the surface. In some embodiments, one or more portions of the inflatable member (240') may be conductive. For example, the entire outer surface of the inflatable member (240') may be conductive or predetermined portions of the inflatable member (240') may be conductive and coupled to the second set of electrodes (230'). As shown in FIG. 2C, the outer surface of the inflatable member may include one more conductive elements (e.g., pattern) (242') having a set of spaced apart conductive stripes extending in a proximal-to-distal direction between the ends of the inflatable member (240'). The one or more conductive elements (242') may be electrically isolated from each other. The conductive stripes may be formed by techniques such as masked electrodeposition. In some embodiments, the conductive element (242') may be disposed symmetrically on the inflatable member (240'). Each of the stripes of the conductive element (242') may be electrically coupled to the distal electrode (230'). The stripes may intersect each other at proximal and distal ends of the inflatable member (240') and/or between the ends of the inflatable member (240'). The inflatable member (240') may be flexible and/or expandable between the metal stripes of the conductive element (242'). The conductive element (242') may be disposed (e.g., deposited) on the inflatable member (240') in a manner that maintains electrical coupling with an electrical lead in the first configuration, second configuration, and configurations in-between. The conductive element (242') may provide rigidity and/or stiffness to the inflatable member (240') and aid in advancement of the inflatable member (240') through vasculature. In some embodiments, the conductive element (242') may include one or more spiral shaped metal portions. In some embodiments, the conductive element (242') may include an interlaced structure (e.g., mesh shape). For example, the interlaced structure may form a set of polygonal apertures (e.g., openings) including one or more of a circular shape, parallelogram, hexagonal, and the like.

Figure 2D:
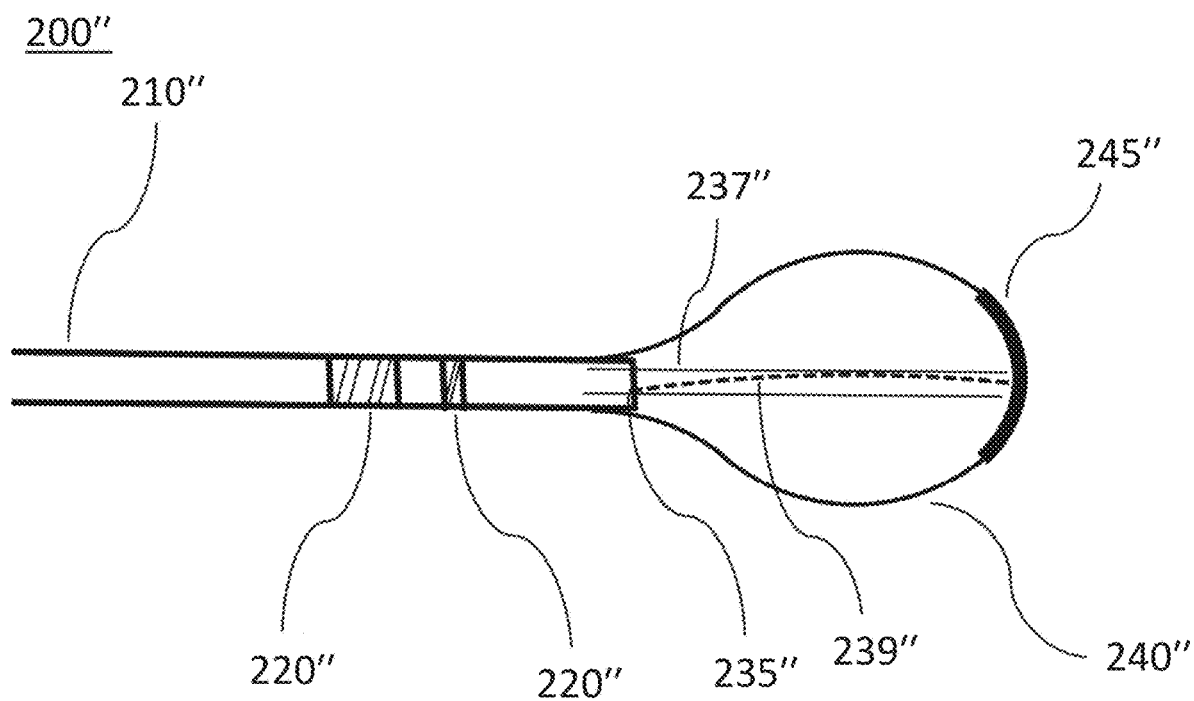

As shown in FIG. 2D, an ablation device (200") may include a catheter shaft (210") coupled at a distal end to an inflatable member (e.g., balloon) (240"). A first set of electrodes (220") may be disposed on an outer surface of the catheter shaft (210"). A second set of electrodes (235") may be disposed on an inner surface of the catheter shaft (210"). In some embodiments, one or more portions of the inflatable member (240") may include a metal electrode portion (245") (e.g., second electrode). In some embodiments, the second electrode (245") is the only electrode formed on the outer surface of the inflatable member. A portion (245") of the inflatable member surface (240") may be metal. For example, a portion (245") of the inflatable member (240") may be a distal portion. In some embodiments, the inflatable member (240") may define an inflatable member lumen (237") extending along a first longitudinal axis of the catheter shaft (210") to a distal end of the inflatable member (240"). A proximal end of an electrical lead (239") may couple to the distal electrode (235") and extend through the inflatable member lumen (237") to couple to the electrode portion (245") at a distal end of the inflatable member (240"). Accordingly, the electrode portion (245") may be configured to deliver irreversible electroporation voltage pulses. In some embodiments, the portion (245") (e.g., formed of metal) of the inflatable member (240") may be configured as an electrode of one polarity while the first set of electrodes (220") (e.g., proximal electrode(s)) may be configured as electrode(s) of the opposite polarity.

In some embodiments, a metallized outer surface of the inflatable member as discussed herein may be further covered by a layer of biocompatible material. The biocompatible coating may help prevent fibrin deposition due to high voltage energy delivery to tissue by the ablation device. In this configuration, a bipole may be formed between the outer surface of the inflatable member and the first set of electrodes (e.g., proximal electrode). However, the ablation device may be configured to deliver energy using one or more biphasic waveforms capacitively across the biocompatible coating on the inflatable member.

In some embodiments, the ablation device (200) may not include a second set of electrodes (230) (e.g., distal electrode) disposed on an outer surface of the catheter shaft (210). Instead, the inflatable member (240) may be configured to include an inner and outer metallized surface that sandwiches the inflatable member (240). The inner and outer metallized surface may include any combination of conductive elements (242) described herein. An electrical lead may be directly connected to the inner metallized surface of the inflatable member (240). In this configuration, a bipole may be formed between the inflatable member (240) and the first set of electrodes (220).

Activation of the first and second sets of electrodes using a predetermined configuration of the inflatable member may provide targeted and precise focal ablation by controlling a focal ablation spot size based on the expansion of the inflatable member. As described herein, focal ablation of tissue may be used to treat ventricular arrhythmia. For example, when the inflatable member of the ablation device is partially filled with saline, a high intensity electric field having a relatively smaller/more focused diameter results in a focal ablation lesion that is relatively smaller in diameter and shallower in depth. When the inflatable member of the ablation device is in the second configuration (e.g., full inflation state), a relatively larger and more dispersed electric field is generated, resulting in a focal ablation lesion that is relatively wider and deeper. In this manner, by varying the extent of expansion of the inflatable member, the depth and/or size of the lesion may be controlled with a single ablation device. Such aspects are useful for creating multiple lesions of varying sizes and/or depths using the same ablation device. Saline may be used to inflate the inflatable member and is not used for conduction. If the inflatable member (which is non-porous) is punctured or otherwise breaks, the saline may safely leak out of the inflatable member.

In some embodiments, a distal end of the catheter shaft (210) may extend into an internal cavity of the inflatable member (240) to provide rigidity and support to a distal end of the ablation device (200) that may aid in advancement of the ablation device (200) through vasculature. The added rigidity may further provide additional tactile feedback to an operator. For example, a distal end of the catheter shaft (210) coupled to a distal end of the inflatable member (240) may provide sufficient support and rigidity in advancing the inflatable member (240) through a transseptal puncture. In some embodiments, the distal end of the catheter shaft (210) may include a set of splines within the inflatable member that bias away from a longitudinal axis of the catheter shaft (210) and connect together at a distal end of the inflatable member (240). For example, the set of splines may be coupled to the catheter shaft (210) and an inner surface of the inflatable member (240) and configured for translation along the longitudinal axis to transition between a first configuration where the set of splines are approximately parallel to the longitudinal axis and a second configuration where the set of splines bias away from the longitudinal axis. The set of splines may form a basket-like shape to provide rigidity and support to the inflatable member. In some embodiments, the distal end of the catheter shaft (210) may be configured with a predetermined stiffness different from the stiffness of the catheter shaft (210) proximal to the inflatable member (240). For example, the distal end of the catheter shaft (210) within the inflatable member (240) may be stiffer than deflectable portions of the catheter shaft (210).

In some embodiments, one or more distal portions of the catheter shaft (210) may include a radiopaque portion. For example, the distal portion of the catheter shaft (210) may include a radiopaque platinum coil within a cavity of the inflatable member (240). The radiopaque portion may be fluoroscopically imaged to aid an operator in locating and positioning the ablation device (200) within one or more body cavities of the patient. The radiopaque portion may include a set of marker bands. In some embodiments, one or more splines of the distal portion (e.g., distal end) of the catheter shaft (210) may include a radiopaque portion (not shown) formed on a surface of that spline. Additionally or alternatively, a location sensor may be coupled to the distal end of the catheter shaft (210) within the inflatable member (240).

Figure 3:
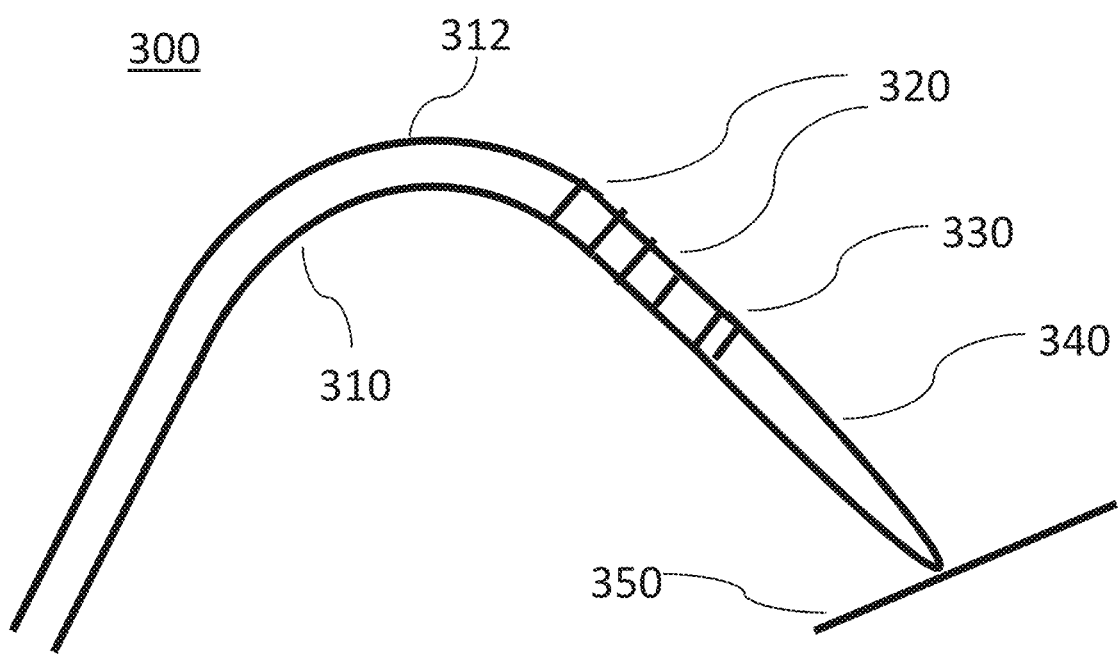
FIG. 3 is a side view of an ablation device, according to other embodiments.

FIG. 3 is a side view of another embodiment of an ablation device (300) (e.g., structurally and/or functionally similar to the ablation device (110, 200)) including a catheter shaft (310) having a first set of electrodes (320) provided proximal to a second set of electrodes (330) and an inflatable member (e.g., balloon) (340). The first set of electrodes may be formed on a surface of a distal portion of the catheter shaft (310). During use, the electrodes (320, 330) may be disposed in a ventricle in order to deliver a pulse waveform to ablate tissue (350), as described in more detail herein.

In some embodiments, a handle (not shown) may be coupled to a proximal portion of the ablation device (300) and may include a bending mechanism (e.g., one or more pull wires (not shown)) configured to modify the shape of the distal portion of the catheter shaft (310). For example, operation of a pull wire of the handle may increase or decrease a curvature in a deflectable portion (312) (e.g., bend in the catheter shaft (310)) in the distal portion of the catheter shaft (310). In some embodiments, the catheter (300) may have a deflectable portion (312) proximal to the second set of electrodes (330) and/or the first set of electrodes (320). The deflectable portion may be configured to deflect up to about 210 degrees relative to the longitudinal axis of the catheter shaft (310). The curvature in the deflectable portion (312) of the catheter shaft (310) may be modified to allow the electrodes (320, 330) and inflatable member (340) to be disposed near and/or in contact with a tissue surface (350) (e.g., in contact with an inner radial surface of a ventricle). In this manner, apposition of the ablation device (300) to tissue may be provided at a desired position and orientation (e.g., the inflatable member may be perpendicular, angled, or parallel to the tissue surface).

In some embodiments, the pulse waveform may be applied between the first set of electrodes (320) and the inflatable member (340) configured in anode and cathode sets. It should be appreciated that any of the pulse waveforms disclosed herein may be progressively or sequentially applied to the set of anode-cathode pairs. In some embodiments, the first set of electrodes (320) may have an opposite polarity to the second set of electrodes (330) during delivery of a voltage pulse waveform. The electrodes (320, 330) may include a series of metallic bands or rings and in some embodiments may be independently addressable. In some embodiments, the electrical leads of at least two electrodes of the first set of electrodes (320) may be electrically coupled at or near a proximal portion of the ablation device, such as, for example, within the handle.

Figure 5A:
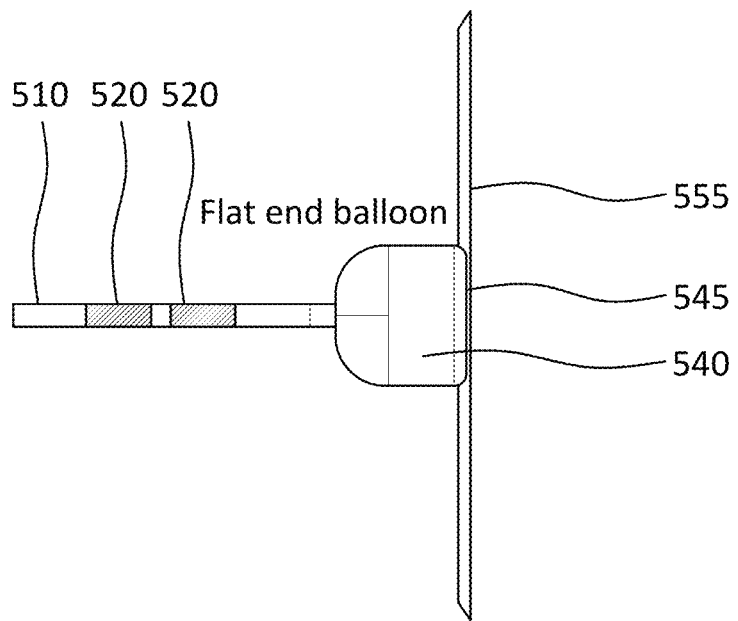
Figure 5B:
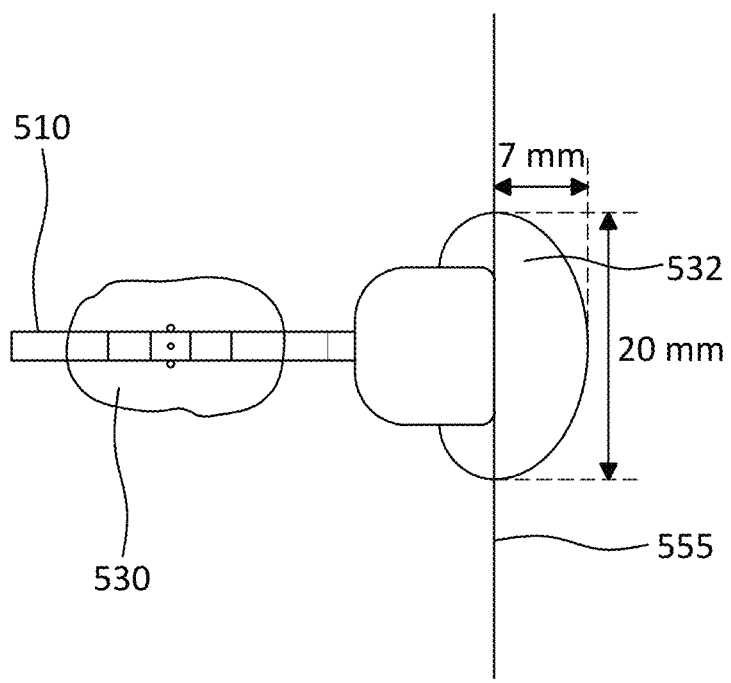

FIG. 5A is a side view of an ablation device (500) (e.g., structurally and/or functionally similar to the ablation device (110)) including a catheter shaft (510) and an inflatable member (e.g., balloon) (540) coupled to a distal end of the catheter shaft (510). In some embodiments, the ablation device (500) is useful for forming lesions on endocardial surfaces (555) via focal ablation. FIG. 5B illustrates spatial zones (530, 532) that may correspond to tissue ablation zones of sufficiently high electric field intensities to generate focal ablation lesions on a tissue surface (555). As shown in FIG. 5A, the inflatable member (540) may generally have a portion (545) that may be configured as a second electrode and which may be at least partly metallic. In some embodiments, the first set of electrodes (520) of the ablation device (500) may be configured as cathodes and the second electrode (545) may be configured as an anode, or vice versa. In some embodiments, the first set of electrodes (520) may have an opposite polarity to the second electrode (545) during delivery of a voltage pulse waveform. The first set of electrodes (520) may be formed on a surface of a distal portion of the catheter shaft (510). The flat distal second electrode (545) of the inflatable member (540) may be disposed against a tissue surface, such as a ventricular wall (555). The inflatable member (540) in the second configuration may have a circular cross-section. For example, the inflatable member (545) may have a diameter of about 12 mm and a voltage potential difference of about 2,000 V may be applied between the anode (520) and cathode (545) electrodes. In some embodiments, the first set of electrodes (520) may have a width of about 3 mm each and a separation of about 3 mm between adjacent electrodes. In some embodiments, the most distal electrode of the first set of electrodes (520) may be separated from the inflatable member (540) by at least about 5 mm.

FIG. 5B illustrates first and second spatial zones (530, 532) corresponding to an electric field intensity of magnitude of at least about 460 V/cm when a potential difference of about 2,000 V is applied between the anode (520) and cathode (545) electrodes with the distal flat electrode (545) disposed against the tissue wall (555). The second spatial zone (532) overlapping the tissue wall (555) may have a depth of about 7 mm and a width of about 20 mm.

Figure 5C:
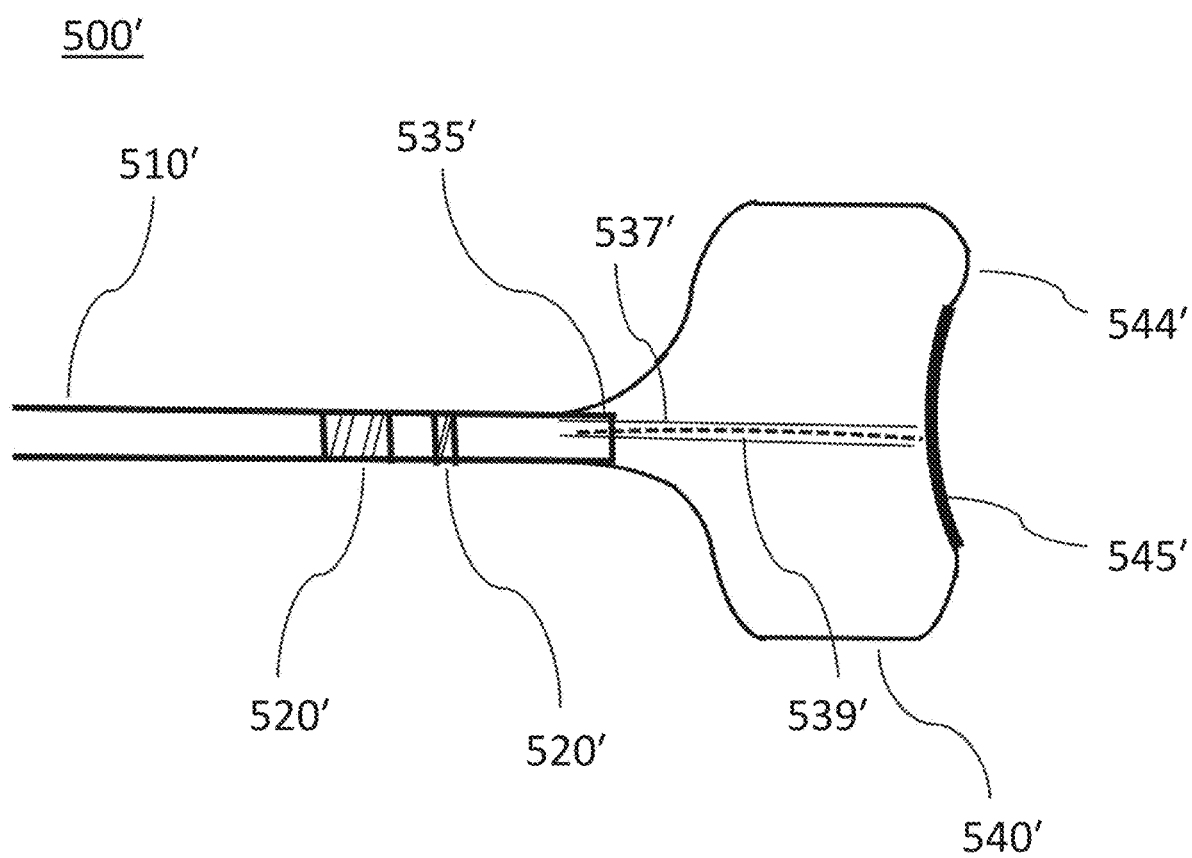
Figure 5D:
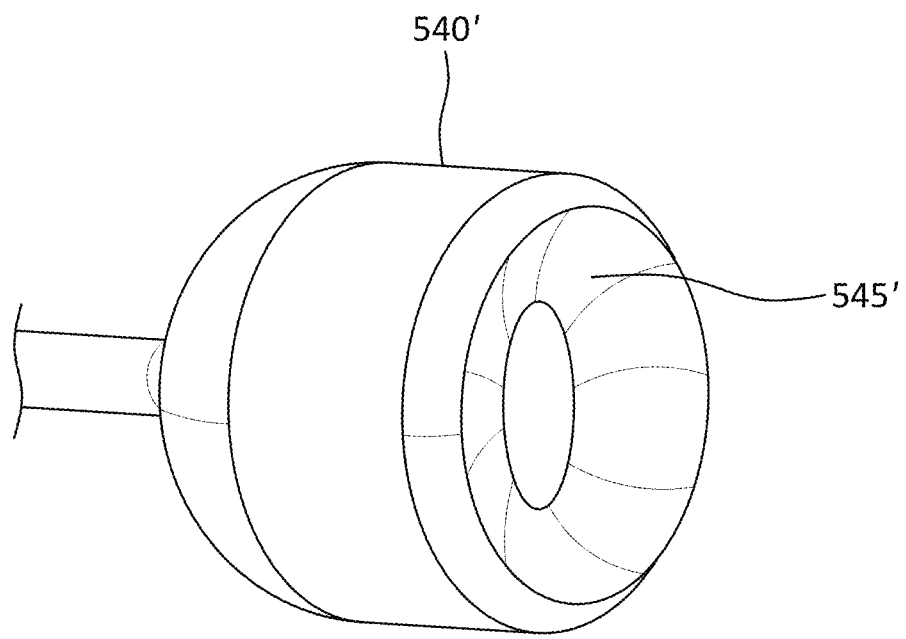

In some embodiments, an ablation device (500') may include an inflatable member (540') having a distal portion having a concave surface facing away from a proximal end of the inflatable member (540'). As shown in FIGS. 5C and 5D, an inflatable member (540') may include a first curved portion (544') and a second curved portion (545'). The first curved portion (544') may include a portion of the inflatable member (540') configured to be in contact with an endocardial surface (555') as shown in FIG. 5E.

In some embodiments, for example as shown in FIG. 5C, the inflatable member (540') may include an inflatable member lumen (537') extending along a first longitudinal axis of the catheter shaft (510') from a distal end of the catheter shaft (510') to a distal end of the inflatable member (540'). A proximal end of an electrical lead (539') may couple to a second set of electrodes (535') (e.g., distal electrode) and extend through the inflatable member lumen (537') to couple to the electrode portion (545') at a distal end of the inflatable member (540'). Accordingly, the electrode portion (545') may be configured to deliver irreversible electroporation voltage pulses. The first set of electrodes (520') and the portion (545') may be configured with opposite polarities.

FIG. 5D is a perspective view of the inflatable member (540') of FIG. 5C having a metallic concave portion (545') covering substantially an entire distal surface of the inflatable member (540'). For example, the inflatable member (545') may have a diameter of about 12 mm and, for example, a voltage potential difference of about 2,000 V may be applied between the inflatable member (545') (e.g., anode) and the first set of electrodes (520') (e.g., cathodes). In some embodiments, the first set of electrodes (520') may have a width of about 3 mm and a separation of about 3 mm between them. The distal-most electrode of the first set of electrodes (520') may be separated from the inflatable member (540') by about 5 mm. The first set of electrodes (520') have a width of about 3 mm and a separation of about 3 mm between them. The most distal electrode of the first set of electrodes (520') may have a separation of about 7 mm from the inflatable member (540'). These dimensions are provided as examples for illustrative purposes only and other values may be chosen for these as found convenient for the clinical application.

Figure 5E:
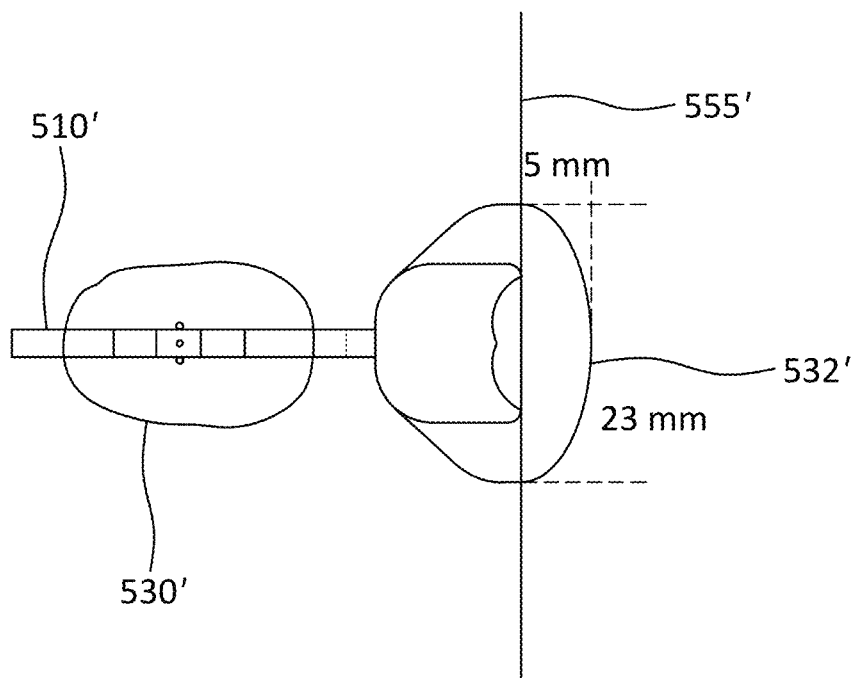

FIG. 5E illustrates first and second spatial zones (530', 532') corresponding to an electric field intensity sufficient to generate focal ablation lesions. The second ablation zone (532') may correspond to a tissue ablation zone when the inflatable member (540') is disposed against the tissue wall (555'). In some embodiments, the second set of electrodes (535') and portion (545') (e.g., comprising metal) of the inflatable member (540') may be configured as an electrode of one polarity while the first set of electrodes (520') (e.g., proximal electrode(s)) may be configured as electrode(s) of the opposite polarity. FIG. 5E illustrates first and second spatial zones (530', 532') corresponding to an electric field intensity having a magnitude of at least about 460 V/cm when a potential difference of about 2,000 V is applied between the anode (520') and cathode (545') electrodes with the distal curved electrode portion (545') (e.g., concave) disposed against the tissue wall (555'). The second spatial zone (532') overlapping the tissue wall (555') may have a depth of about 5 mm and a width of about 21 mm. In some variations, the second spatial zone (532') may have a depth of up to about 10 mm and a width of up to about 30 mm.

Figure 5F:
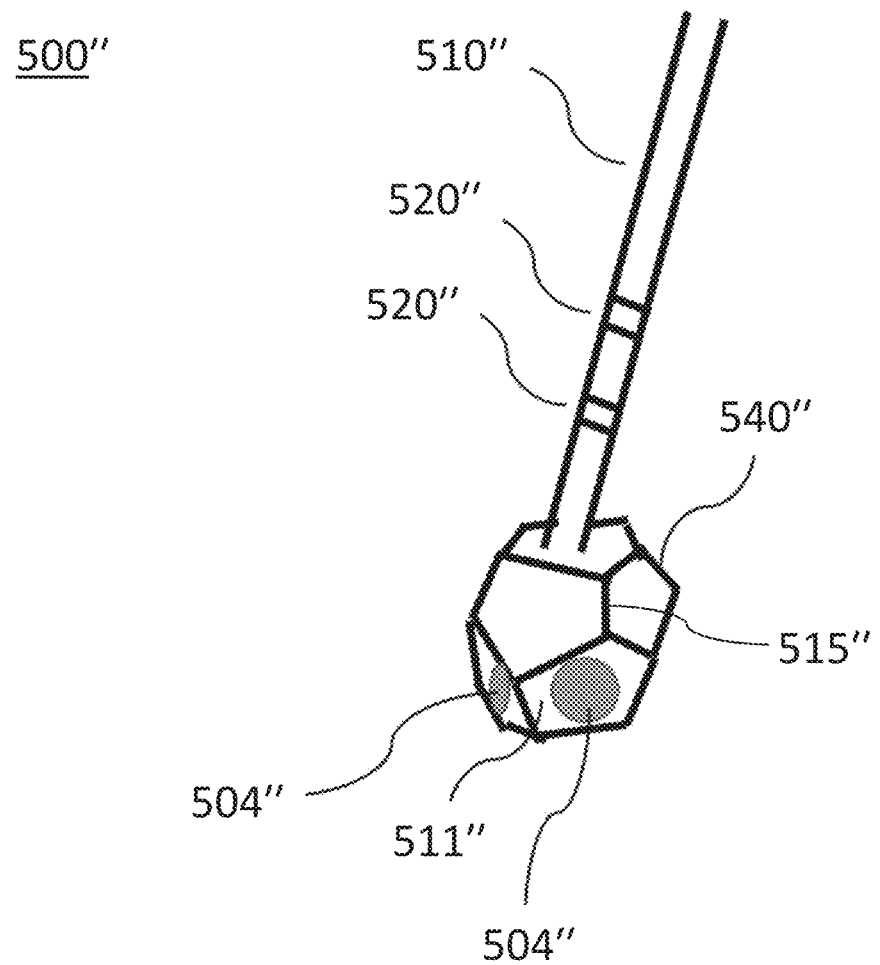
Figure 5G:
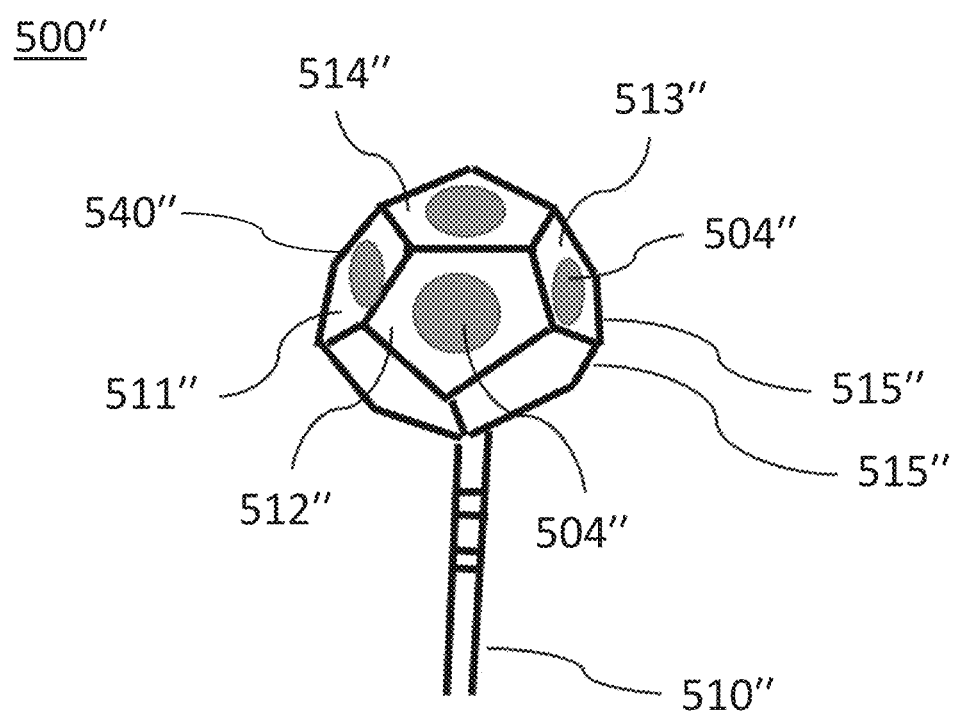

FIGS. 5F and 5G illustrate an ablation device (500") (e.g., structurally and/or functionally similar to the ablation device (110)) including a catheter shaft (510") and an inflatable member (540") coupled to a distal end of the catheter shaft (510"). In some embodiments, the ablation device (500") is useful for forming lesions on endocardial surfaces via focal ablations. In some embodiments, the inflatable member (540") may have a multi-faceted shape. In some embodiments, the multi-faceted shape may generally be a polyhedral shape with one or more second electrodes (504") disposed on portions of one or more faces (511") of the polyhedron. A first set of electrodes (520") may be disposed on the catheter shaft (510"). The inflatable member (540") may generally have one or more second electrode portions (504") that may be configured as an electrode of the second set of electrodes and which may include metal. The inflatable member (540") in the second configuration may have a polyhedron shape with one or more faces (511"). The second electrode portions (504") may be electrically wired together to function as a single electrode or wired separately as independent electrodes. FIG. 5F illustrates a dodecahedron-shaped inflatable member (540") having second electrode portions (504") on six of the faces (511"). In some embodiments, the first set of electrodes (520") may have an opposite polarity to the second electrode portions (504") during delivery of a voltage pulse waveform. In some embodiments, one or more faces (511") of the polyhedron may have a curved face.

In some embodiments, one or more of the second electrode portions (504") of the second set of electrodes may be configured to receive ECG signals, as described herein. The strength and/or pattern of the ECG signal received by the one or more second electrode portions (504") may be used to determine a level of contact each of the second electrode portions (504") has with tissue (e.g., cardiac chamber wall). A set of the second electrode portions (504") may be selected using the ECG signals to be configured as an anode or cathode. Thus, one or more second electrode portions (504") disposed on corresponding faces (511") of the inflatable member (540") may be used for tissue ablation based on an ECG signal strength corresponding to tissue contact. In some embodiments, the edges of the faces (511") (e.g., polyhedral surfaces) may be rounded so as to form a "soft" face.

In some embodiments, one or more of the second set of electrodes (504") disposed on a face (511") may include a concave curved shape (e.g., the electrodes may be indented) such that those faces (511") may form a pocket configured to contact a tissue surface. The edges (515") of these faces (511") may have a higher stiffness than the faces (511") themselves such that the inflatable member (540") in the second configuration may form a polyhedron shape having one or more indented faces (511").

Figure 5H:
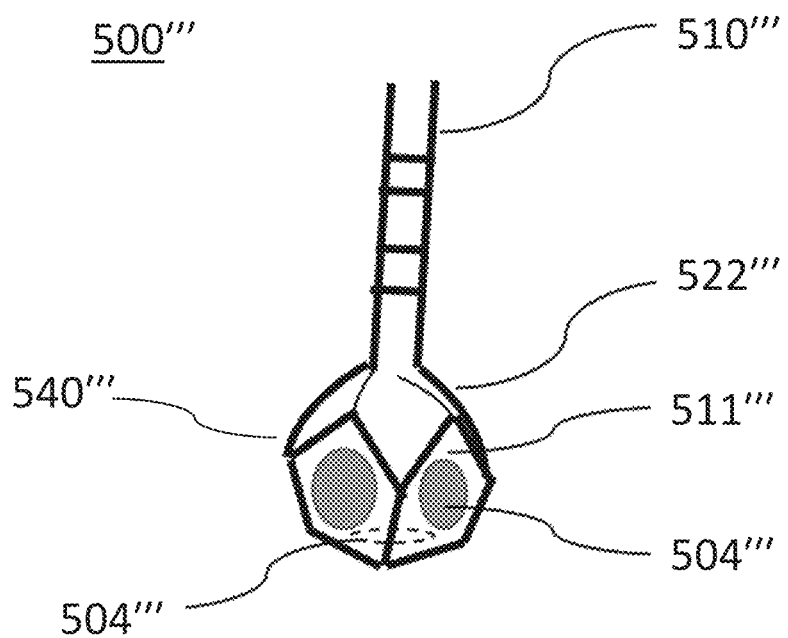
Figure 51:
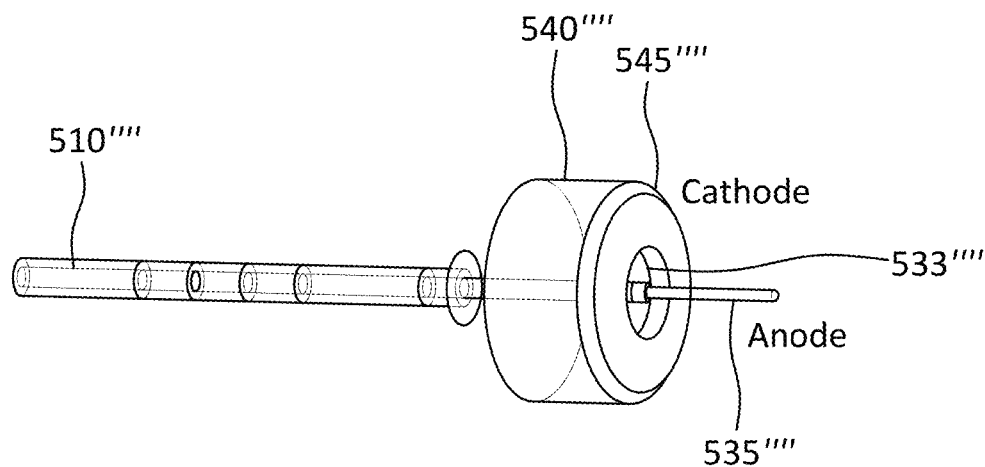

FIG. 5G is another perspective view of the ablation device (500") having an inflatable member (540") having a generally polyhedron shape with metallized electrodes (504") disposed on a portion of one or more faces (511", 512", 513", 514") of the inflatable member (540"). In some embodiments, a catheter shaft (510") may define a catheter shaft lumen (not shown) configured for saline infusion to inflate the inflatable member (540"). Electrical leads may also be disposed within the catheter shaft lumen and configured to connect to the one or more electrodes (504"). Edges (515") of the faces (511", 512", 513", 514") may be rounded and have a higher stiffness than a surface of the face so as to form an indented face surface when in the second configuration. In some embodiments, the diameter of the inflatable member (540") in the second configuration may be between about 6 mm and about 22 mm. The first set of electrodes (520") may be separated by at least about 3 mm or more from a proximal end of the inflatable member (540"). The metallized electrode portions (504") may have a diameter between about 6 mm and about 15 mm. In some embodiments, the edges (522''') of one or more faces (511''') of the inflatable member (540''') may be curved. As shown in FIG. 5H, one or more electrode portions (504''') of the second set of electrodes may be disposed on a face (511''') of the inflatable member (540'''). The curved edges (522''') (e.g., polyhedral surface) may form a soft face (511''').

FIG. 5I illustrates an ablation device (500"") (e.g., structurally and/or functionally similar to the ablation device (110)) including a catheter shaft (510"") and an inflatable member (e.g., balloon) (540"") coupled to a distal end of the catheter shaft (510""). In some embodiments, the ablation device (500"") is useful for forming lesions on endocardial surfaces via focal ablation. In some embodiments, the inflatable member (540"") may define an annular inflatable member lumen (533"") (e.g., having an annular shape) and include a distal face (545"") with a first electrode portion. The distal face (545"") may have a substantially planar portion. A second electrode (535"") (e.g. needle) may be disposed within the inflatable member lumen (533"") and may extend out from, and distal to, the inflatable member lumen (533"") along a longitudinal axis of the inflatable member (540""). The inflatable member (540"") may have a flat distal face (545"") that may be metallized and configured as the first electrode. The annular space defined by the inflatable member lumen (533"") may separate the second electrode (535"") from the annular inflatable member (540"") to prevent flash arcing when the second electrode (535"") and the first electrode portion (545"") are polarized with opposite electrical polarities. For example, the needle may have a length between about 8 mm and about 10 mm. The inflatable member (540"") may have a diameter of about 12 mm. The inflatable member lumen (533"") may have a diameter between about 4 mm and about 8 mm.

Figure 5J:
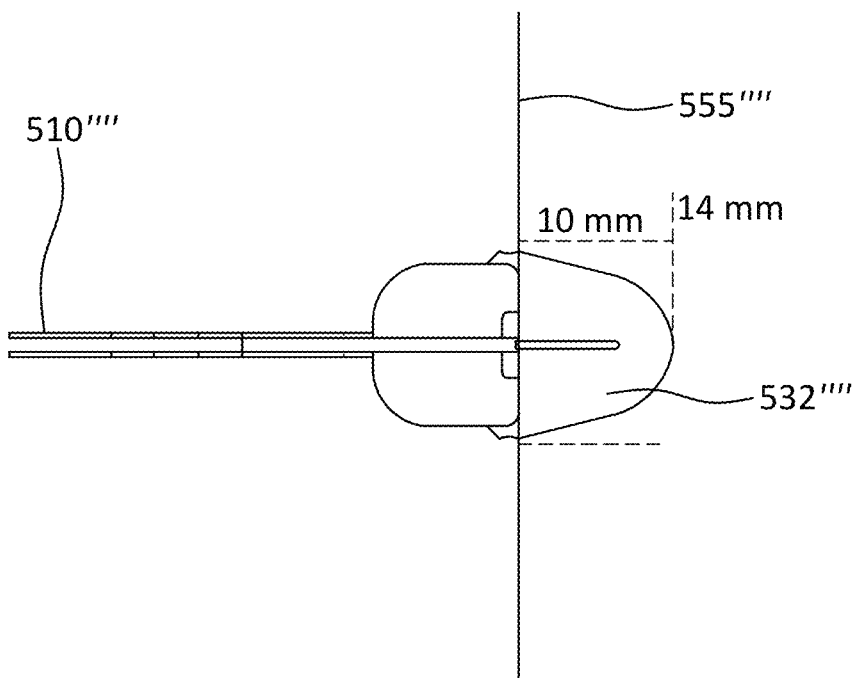

FIG. 5J illustrates a spatial zone (532"") corresponding to an electric field intensity of magnitude of at least about 460 V/cm when a potential difference of about 2,000 V is applied between the electrode (535"") and electrode portions (545"") with the flat distal electrode (545"") disposed against the tissue wall (555""). The spatial zone (532"") overlapping the tissue wall (555"") may have a depth of about 10 mm and a width of about 14 mm.

Figure 11:
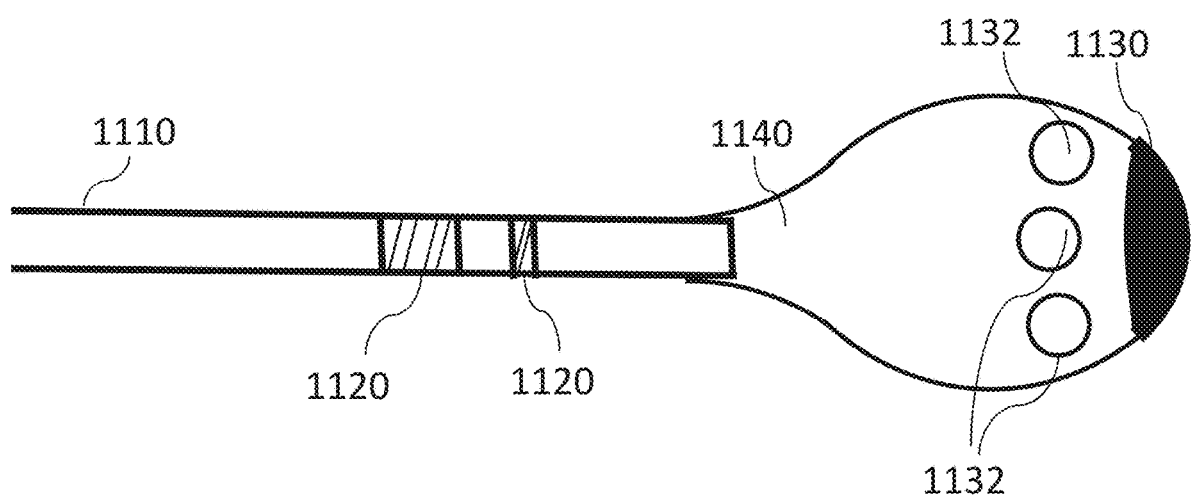
FIG. 11 is a side view of an ablation device, according to other embodiments.

FIG. 11 is a side view of another embodiment of an ablation device (1100) (e.g., structurally and/or functionally similar to the ablation device (110, 200, 300, 500, 500', 500", 500"") including a catheter shaft (1110) having a first set of electrodes (1120) provided proximal to a second set of electrodes (1130, 1132) and an inflatable member (e.g., balloon) (1140). The first set of electrodes (1120) may be formed on a surface of a distal portion of the catheter shaft (1110). That is, the first set of electrodes (1120) may be formed on a surface of the distal end of the catheter shaft (1110). The second set of electrodes (1130, 1132) may be formed on a surface of a distal end of the inflatable member (1140) and may be electrically isolated from the first set of electrodes (1120). In some embodiments, a major axis (e.g., longitudinal axis) of the second electrodes (1132) may be substantially parallel to the longitudinal axis of the catheter shaft (1110) and/or inflatable member (1140).

In some embodiments, the ablation device (1100) is useful for forming lesions on endocardial surfaces via focal ablation, such as an inner surface of a ventricle. During use, the electrodes (1120, 1130, 1132) may be disposed in a ventricle in order to deliver a pulse waveform to ablate tissue, as described in more detail herein. A distal portion of the inflatable member (1140) may include and/or be formed in an atraumatic shape that reduces trauma to tissue (e.g., prevents and/or reduces the possibility of tissue puncture). The catheter shaft (1110) and inflatable member (1140) may be sized for advancement into an endocardial space (e.g., left ventricle). The catheter shaft (1110) may be flexible so as to be deflectable. For example, a deflectable portion of the catheter shaft (1110) may be configured for deflecting a portion of the catheter (1100) including the second set of electrodes (1130, 1132) and the inflatable member (1140) up to about 210 degrees relative to the longitudinal axis. The inflatable member (1140) may be configured to transition between a first configuration (e.g., deflated state) and a second configuration (e.g., inflated state). In the first configuration, the inflatable member (1140) may have a diameter that is about the same as a diameter of the catheter shaft (1110) to aid in advancing the ablation device (1100) through vasculature. For example, the inflatable member (1140) in the first configuration may be approximately parallel to a longitudinal axis of the catheter shaft (1110). The inflatable member (1140) in the second configuration may bias away from the longitudinal axis. The first set of electrodes (1120) may be structurally and/or functionally similar to the electrodes (220, 230) described with respect to FIGS. 2A-2D.

The first set of electrodes (1120) may be electrically coupled together using one or more electrical leads. The second set of electrodes (1130, 1132) may be electrically coupled together using a different set of electrical leads. In some embodiments, the inflatable member (1140) may be electrically coupled to the second set of electrodes (1130, 1132). A voltage pulse waveform delivered between the first set of electrodes (1120) and the inflatable member (1140) electrically coupled to the second set of electrodes (1130, 1132) may be used to form a lesion via focal ablation (e.g., a spot lesion) of a predetermined size and shape. In some embodiments, the first set of electrodes (1120) may be configured as an anode while the second set of electrodes (1130, 1132) and inflatable member (240) may be configured as a cathode, or vice versa. Accordingly, a bipole may be formed between the first set of electrodes (1120) and the inflatable member (1140) that results in an electric field capable of ablating tissue (e.g., myocardial cells on an inner surface or within a ventricle). The inflatable member (1140) and the first set of electrodes (1120) may be electrically isolated from each other. For example, the second set of electrodes (1130, 1132) and the first set of electrodes (1120) may each couple to a respective insulated electrical lead, with each lead having sufficient electrical insulation to sustain an electrical potential difference of at least 700 V across its thickness without dielectric breakdown.

The first and second sets of electrodes (1120, 1130, 1132) may include an atraumatic shape to reduce trauma to tissue. For example, the first set of electrodes (1120) may be ring electrodes. In some embodiments, the first set of electrodes (1120) may be located along any portion of the catheter shaft (1110) proximal to the second set of electrodes (1130, 1132). The first set of electrodes (1120) may be spaced apart from each other and wired together via one or more insulated leads so as to function as a single electrode (e.g., anode or cathode) while allowing the catheter shaft (1110) to remain flexible and facilitate deflection. The second set of electrodes (1130, 1132) may be disposed on a surface of the inflatable member (1140) and/or flush with the surface of the inflatable member (1140) so as to be electrically coupled to the inflatable member (1140). The second set of electrodes (1130, 1132) may have the same or different sizes, shapes, and/or location along the inflatable member (1140).

For example, the second set of electrodes (1130, 1132) may include a distal tip electrode (1130) and a set of generally circular or elliptically-shaped electrodes (1132) disposed around a circumference of the inflatable member (1140). For example, the second set of electrodes (1130) may be formed on the inflatable member (1140) on an approximate plane approximately perpendicular to the longitudinal axis. In some embodiments, each electrode of the second set of electrodes (1130, 1132) may be wired together. In other embodiments, subsets of the electrodes of the second set of electrodes (1130, 1132) may be electrically wired together while other subsets may be independently addressable. In some embodiments, the distal tip electrode (1132) may be electrically isolated from the first set of electrodes (1120). In some embodiments, each electrode of the second set of electrodes (1130, 1132) may be independently addressable. The distal tip electrode (1132) may be formed at a distal portion of the inflatable member (1440) and electrically isolated from the first set of electrodes (1120). The distal tip electrode (1132) may have a diameter in the range between about 3 mm and about 10 mm In some embodiments, one or more of the electrodes of the first and second sets of electrodes (1120, 1132) may be configured for receiving or sensing an ECG signal for recording electrophysiology data. The ablation device (1100) may include one or more ECG signal electrodes. For example, one or more electrodes of the second set of electrodes (1130, 1132) may be configured to receive an ECG signal. These ECG signal electrodes, such as the distal tip electrode (1130), may be coupled to its own insulated electrical lead. The ECG signal electrode may be electrically isolated from the inflatable member (1140) using, for example, a ring of insulation around the ECG signal electrode. In these embodiments, the ablation device may be used to record electrophysiology data in place of a mapping catheter before and/or after tissue ablation.

One or more of a biphasic signal may be applied to the bipole such that tissue may be ablated between the inflatable member (1140) and the first set of electrodes (1120) at a desired location in the ventricle. In some embodiments, the inflatable member (1140) in the second configuration may be configured to contact endocardial tissue while the first set of electrodes (1130) in the second configuration may not contact endocardial tissue. The electric field generated by the ablation device (1100) due to conduction between the inflatable member (1140) and first set of electrodes (1120) through the blood pool and through tissue may result in focal ablation of tissue via irreversible electroporation. The inflatable member (1140) when inflated may have an asymmetric shape in a proximal-to-distal direction, so that one end (for example the distal end) of the inflatable member (1140) is more bulbous than the other end (for example the proximal end) of the inflatable member (1140). The inflatable member (1140) when inflated may be rotationally symmetric about the longitudinal axis of the catheter shaft (1110). In this configuration, the inflatable member (1140) may be contacting an endocardial surface and used to form a lesion via focal ablation (e.g., a spot lesion).

In some embodiments, the catheter shaft (1110) may include a deflectable portion between the first set of electrodes (1120) and the second set of electrodes (1130) in the same manner as illustrated in FIG. 3. The deflectable portion may be configured to deflect up to about 210 degrees relative to the longitudinal axis of the catheter shaft (1110). In some embodiments, an actuator (e.g., fluid source) may be coupled to the inflatable member and configured to transition the inflatable member between the first configuration (e.g., deflated state) and the second configuration (e.g., inflated state) by, for example, using pressurized saline.

Figure 12:
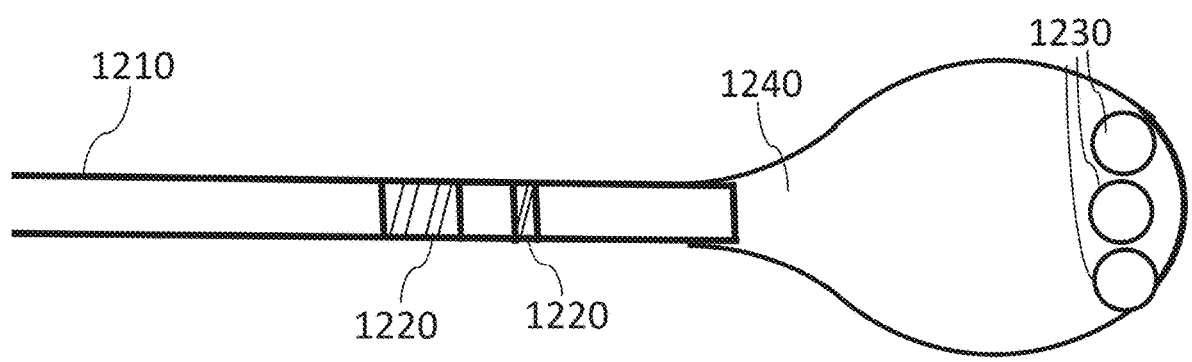
FIG. 12 is a side view of an ablation device, according to other embodiments.

FIG. 12 is a side view of another embodiment of an ablation device (1200) (e.g., structurally and/or functionally similar to the ablation device (110, 200, 300, 500, 500', 500", 500"", 1100) including a catheter shaft (1210) having a first set of electrodes (1220) provided proximal to a second set of electrodes (1230) and an inflatable member (e.g., balloon) (1240). The first set of electrodes (1220) may be formed on a surface of a distal portion of the catheter shaft (1210). That is, the first set of electrodes (1220) may be formed on a surface of the distal end of the catheter shaft (1210). The second set of electrodes (1230) may be formed on a surface of a distal end of the inflatable member (1240) and may be electrically isolated from the first set of electrodes (1220). In some embodiments, the ablation device (1200) is useful for forming lesions on endocardial surfaces via focal ablation, such as an inner surface of a ventricle. During use, the electrodes (1220, 1230) may be disposed in a ventricle in order to deliver a pulse waveform to ablate tissue, as described in more detail herein. A distal portion of the inflatable member (1240) may include and/or be formed in an atraumatic shape that reduces trauma to tissue. The catheter shaft (1210) and inflatable member (1240) may be sized for advancement into an endocardial space (e.g., left ventricle). The catheter shaft (1210) may be flexible so as to be deflectable. For example, a deflectable portion of the catheter shaft (1210) may be configured for deflecting a portion of the catheter (1200) including the second set of electrodes (1230) and the inflatable member (1240) up to about 210 degrees relative to the longitudinal axis. The inflatable member (1240) may be configured to transition between a first configuration (e.g., deflated state) and a second configuration (e.g., inflated state). In the first configuration, the inflatable member (1240) may have a diameter that is about the same as a diameter of the catheter shaft (1210) to aid in advancing the ablation device (1200) through vasculature. For example, the inflatable member (1240) in the first configuration may be approximately parallel to a longitudinal axis of the catheter shaft (1210). The inflatable member (1240) when inflated may bias away from the longitudinal axis. The first set of electrodes (1220) may be structurally and/or functionally similar to the electrodes (220, 230) described with respect to FIGS. 2A-2D.

The first set of electrodes (1220) may be electrically coupled together using one or more electrical leads. One or more of the second set of electrodes (1230) may be electrically coupled together using a different set of electrical leads. A voltage pulse waveform delivered between the first set of electrodes (1220) and the second set of electrodes (1230) may be used to form a lesion via focal ablation (e.g., a spot lesion) of a predetermined size and shape. In some embodiments, the first set of electrodes (1220) may be configured as an anode while the second set of electrodes (1230) may be configured as a cathode, or vice versa. Accordingly, a bipole may be formed between the first set of electrodes (1220) and the second set of electrodes (1230) that results in an electric field capable of ablating tissue (e.g., myocardial cells on an inner surface or within a ventricle). The second set of electrodes (1230) and the first set of electrodes (1220) may be electrically isolated from each other. For example, the second set of electrodes (1230) and the first set of electrodes (1220) may each couple to a respective insulated electrical lead, with each lead having sufficient electrical insulation to sustain an electrical potential difference of at least 700 V across its thickness without dielectric breakdown.

The first and second sets of electrodes (1220, 1230) may include an atraumatic shape to reduce trauma to tissue. For example, the first set of electrodes (1220) may be ring electrodes. In some embodiments, the first set of electrodes (1220) may be located along any portion of the catheter shaft (1210) proximal to the second set of electrodes (1230). The first set of electrodes (1220) may be spaced apart from each other and wired together via one or more insulated leads so as to function as a single electrode (e.g., anode or cathode) while allowing the catheter shaft (1210) to remain flexible and facilitate deflection. The second set of electrodes (1230) may be disposed on a surface of the inflatable member (1240) and/or flush with the surface of the inflatable member (1240) so as to be electrically coupled to the inflatable member (1240). The second set of electrodes (1230) may have the same or different sizes, shapes, and/or location along the inflatable member (1240).

For example, the second set of electrodes (1230) may include a set of generally circular electrodes disposed around a circumference of the inflatable member (1240). In some embodiments, each electrode of the second set of electrodes (1230) may be wired together. In other embodiments, subsets of the electrodes of the second set of electrodes (1230) may be electrically wired together while other subsets may be independently addressable.

In some embodiments, one or more of the electrodes of the first and second sets of electrodes (1220) may be configured for receiving or sensing an ECG signal for recording electrophysiology data. The ablation device (1200) may include one or more ECG signal electrodes. For example, one or more electrodes of the second set of electrodes (1230) may be configured to receive an ECG signal. These ECG signal electrodes may be coupled to their own insulated electrical lead. In these embodiments, the ablation device may be used to record electrophysiology data in place of a mapping catheter before and/or after tissue ablation.

One or more of a biphasic signal may be applied to the bipole formed by the first set of electrodes (122) and the second sets of electrodes (1230) such that tissue distal to or around the inflatable member (1240) may be ablated at a desired location in the ventricle. For example, a biphasic pulse waveform may be delivered between the sets of electrodes, resulting in a zone of irreversible electroporation ablation in the region around the inflatable member. The inflatable member (1240) when inflated may have an asymmetric shape in a proximal-to-distal direction, so that one end (for example the distal end) of the inflatable member (1240) is more bulbous than the other end (for example the proximal end) of the inflatable member (1240). The inflatable member (1240) when inflated may be rotationally symmetric about the longitudinal axis of the catheter shaft (1210). In this configuration, the inflatable member (1240) may be placed at an endocardial surface and used to form a lesion via focal ablation (e.g., a spot lesion). The electrode leads may be configured with sufficient insulation and high dielectric strength to be suitable for delivery of irreversible electroporation energy as described herein.

In some embodiments, the catheter shaft (1210) may include a deflectable portion between the first set of electrodes (1220) and the second set of electrodes (1230) in some embodiments, or proximal to the first set of electrodes (1220) in other embodiments. The deflectable portion may be configured to deflect up to about 210 degrees relative to the longitudinal axis of the catheter shaft (1210). In some embodiments, an actuator (e.g., fluid source) may be coupled to the inflatable member and configured to transition the inflatable member between the first configuration (e.g., deflated state) and the second configuration (e.g., inflated state) by, for example, using pressurized saline.

Figure 13:
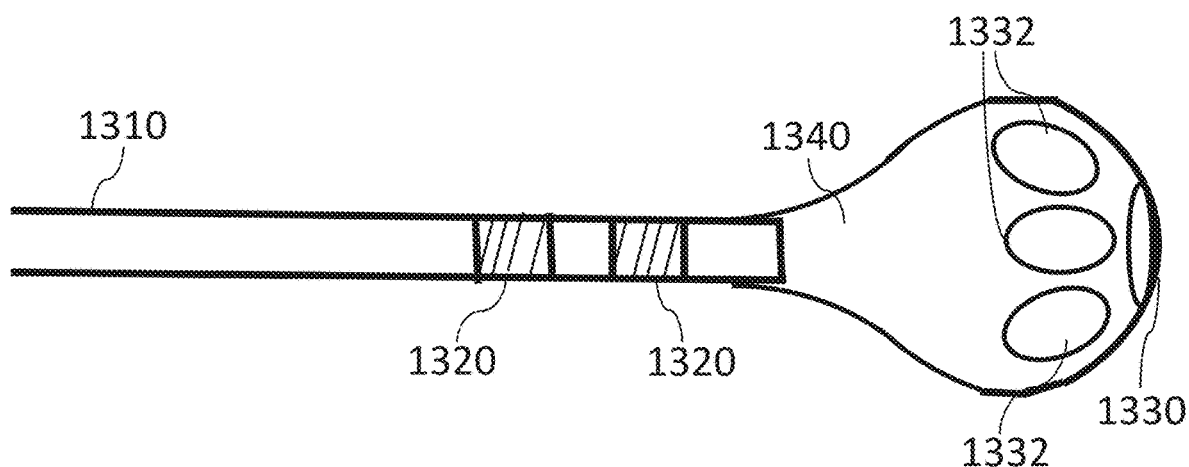
FIG. 13 is a side view of an ablation device, according to other embodiments.

FIG. 13 is a side view of another embodiment of an ablation device (1300) (e.g., structurally and/or functionally similar to the ablation device (110, 200, 300, 500, 500', 500", 500''', 1100, 1200) including a catheter shaft (1310) having a first set of electrodes (1320) provided proximal to a second set of electrodes (1330, 1332) and an inflatable member (e.g., balloon) (1340). The first set of electrodes (1320) may be formed on a surface of a distal portion of the catheter shaft (1310). That is, the first set of electrodes (1320) may be formed on a surface of the distal end of the catheter shaft (1310). The second set of electrodes (1330, 1332) may be formed on a surface of a distal end of the inflatable member (1340) and may be electrically isolated from the first set of electrodes (1320). In some embodiments, a major axis (e.g., longitudinal axis) of the second electrodes (1332) may be substantially parallel to the longitudinal axis of the catheter shaft (1310) and/or inflatable member (1340).

In some embodiments, the ablation device (1300) is useful for forming lesions on endocardial surfaces via focal ablation, such as an inner surface of a ventricle. During use, the electrodes (1320, 1330, 1332) may be disposed in a ventricle in order to deliver a pulse waveform to ablate tissue, as described in more detail herein. A distal portion of the inflatable member (1340) may include and/or be formed in an atraumatic shape that reduces trauma to tissue. The catheter shaft (1310) and inflatable member (1340) may be sized for advancement into an endocardial space (e.g., left ventricle). The catheter shaft (1310) may be flexible so as to be deflectable. For example, a deflectable portion of the catheter shaft (1310) may be configured for deflecting a portion of the catheter (1300) including the second set of electrodes (1330, 1332) and the inflatable member (1340) up to about 210 degrees relative to the longitudinal axis. The inflatable member (1340) may be configured to transition between a first configuration (e.g., deflated state) and a second configuration (e.g., inflated state). In the first configuration, the inflatable member (1340) may have a diameter that is about the same as a diameter of the catheter shaft (1310) to aid in advancing the ablation device (1300) through vasculature. For example, the inflatable member (1340) in the first configuration may be approximately parallel to a longitudinal axis of the catheter shaft (1310). The inflatable member (1340) when inflated may bias away from the longitudinal axis. The first set of electrodes (1320) may be structurally and/or functionally similar to the electrodes (220, 230) described with respect to FIGS. 2A-2D.

The first set of electrodes (1320) may be electrically coupled together using one or more electrical leads. The second set of electrodes (1330, 1332) may be electrically coupled together using a different set of electrical leads. A voltage pulse waveform delivered between the first set of electrodes (1320) and the second set of electrodes (1330, 1332) to form a lesion via focal ablation (e.g., a spot lesion) of a predetermined size and shape. In some embodiments, the first set of electrodes (1320) may be configured as an anode while the second set of electrodes (1330, 1332) may be configured as a cathode, or vice versa. The second set of electrodes (1330, 1332) and the first set of electrodes (1320) may be electrically isolated from each other. For example, the second set of electrodes (1330, 1332) and the first set of electrodes (1320) may each couple to a respective insulated electrical lead, with each lead having sufficient electrical insulation to sustain an electrical potential difference of at least 700 V across its thickness without dielectric breakdown.

The first and second sets of electrodes (1320, 1330, 1332) may include an atraumatic shape to reduce trauma to tissue. For example, the first set of electrodes (1320) may be ring electrodes. In some embodiments, the first set of electrodes (1320) may be located along any portion of the catheter shaft (1310) proximal to the second set of electrodes (1330, 1332). The first set of electrodes (1320) may be spaced apart from each other and wired together via one or more insulated leads so as to function as a single electrode (e.g., anode or cathode) while allowing the catheter shaft (1310) to remain flexible and facilitate deflection. The second set of electrodes (1330, 1332) may be disposed on a surface of the inflatable member (1340) and/or flush with the surface of the inflatable member (1340) so as to be electrically coupled to the inflatable member (1340). The second set of electrodes (1330, 1332) may have the same or different sizes, shapes, and/or location along the inflatable member (1340).

For example, the second set of electrodes (1330, 1332) may include a distal tip electrode (1330) and a set of generally elliptically-shaped electrodes (1332) disposed around a circumference of the inflatable member (1340). For example, the second set of electrodes (1330) may be formed on the inflatable member (1340) on an approximate plane approximately perpendicular to the longitudinal axis. In some embodiments, a longitudinal axis of each of the electrodes (1332) may be substantially parallel to the longitudinal axis of the catheter shaft (1310) and/or inflatable member (1340). In some embodiments, each electrode of the second set of electrodes (1330, 1332) may be wired together. In other embodiments, subsets of the electrodes of the second set of electrodes (1330, 1332) may be electrically wired together while other subsets (e.g., the distal tip electrode) may be independently addressable. In some embodiments, the distal tip electrode (1332) may be electrically isolated from the first set of electrodes (1320). In some embodiments, each electrode of the second set of electrodes (1330, 1332) may be independently addressable. The distal tip electrode (1330) may be formed at a distal portion of the inflatable member (1340) and electrically isolated from the first set of electrodes (1320).

In some embodiments, one or more of the electrodes of the first and second sets of electrodes (1320, 1330, 1332) may be configured for receiving or sensing an ECG signal for recording electrophysiology data. The ablation device (1300) may include one or more ECG signal electrodes. For example, one or more electrodes of the second set of electrodes (1330, 1332) may be configured to receive an ECG signal. These ECG signal electrodes, such as the distal tip electrode (1330), may be coupled to its own insulated electrical lead. In these embodiments, the ablation device may be used to record electrophysiology data in place of a mapping catheter before and/or after tissue ablation.

The inflatable member (1340) when inflated may have an asymmetric shape in a proximal-to-distal direction, so that one end (for example the distal end) of the inflatable member (1340) is more bulbous than the other end (for example the proximal end) of the inflatable member (1340). The inflatable member (1340) when inflated may be rotationally symmetric about the longitudinal axis of the catheter shaft (1310). In this configuration, the inflatable member (1340) may be placed at an endocardial surface and used to form a lesion via focal ablation (e.g., a spot lesion). The electrode leads may be configured with sufficient insulation and high dielectric strength to be suitable for delivery of irreversible electroporation energy as described herein.

In some embodiments, the catheter shaft (1310) may include a deflectable portion between the first set of electrodes (1320) and the second set of electrodes (1330), or proximal to the first set of electrodes (1320). The deflectable portion may be configured to deflect up to about 210 degrees relative to the longitudinal axis of the catheter shaft (1310). In some embodiments, an actuator (e.g., fluid source) may be coupled to the inflatable member and configured to transition the inflatable member between the first configuration (e.g., deflated state) and the second configuration (e.g., inflated state) by, for example, using pressurized saline.

Figure 14:
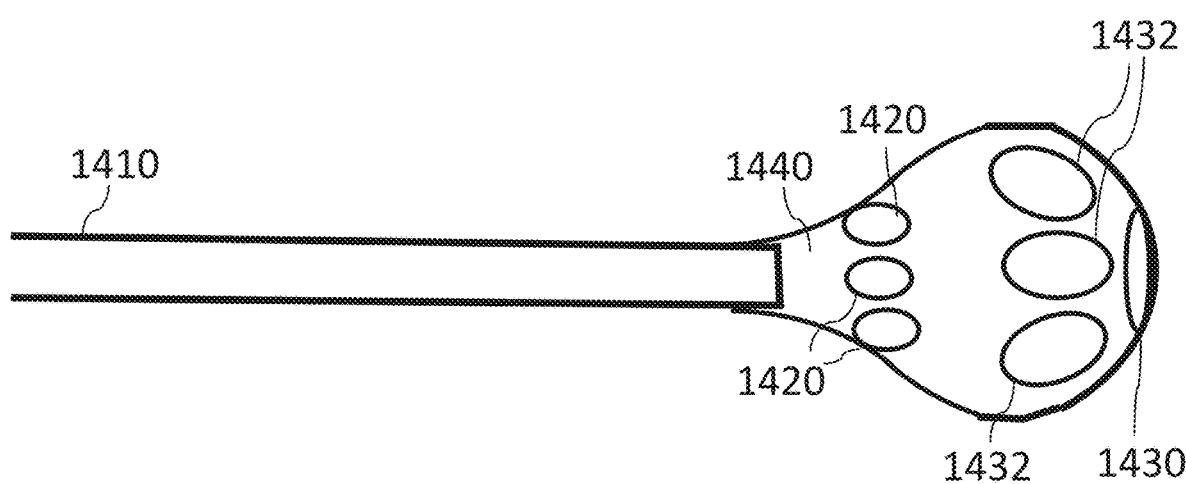
FIG. 14 is a side view of an ablation device, according to other embodiments.

FIG. 14 is a side view of another embodiment of an ablation device (1400) (e.g., structurally and/or functionally similar to the ablation device (110, 200, 300, 500, 500', 500", 500''', 1100, 1200, 1300) including a catheter shaft (1410) having a first set of electrodes (1420) provided proximal to a second set of electrodes (1430, 1432) and an inflatable member (e.g., balloon) (1440). The first set of electrodes (1420) may be formed on a surface of a proximal portion of the inflatable member (1440). For example, the first set of electrodes (1420) may be formed proximal to an equatorial plane of the inflatable member (1440). As used herein, the equatorial plane of the inflatable member (1440) refers to the plane intersecting the maximum cross-sectional diameter of the inflatable member (1440) when inflated. That is, a proximal portion of the inflatable member (1440) is proximal to a cross-sectional diameter of the inflatable member (1440) at its largest portion. The second set of electrodes (1430, 1432) may be formed on a surface of the inflatable member (1440) distal to the equatorial plane and may be electrically isolated from the first set of electrodes (1420). In some embodiments, a major axis (e.g., longitudinal axis) of the first set of electrodes (1420) and the second set of electrodes (1432) may be substantially parallel to the longitudinal axis of the catheter shaft (1410) and/or inflatable member (1440).

In some embodiments, the ablation device (1400) is useful for forming lesions on endocardial surfaces via focal ablation, such as an inner surface of a ventricle. During use, the electrodes (1420, 1430, 1432) may be disposed in a ventricle in order to deliver a pulse waveform to ablate tissue, as described in more detail herein. A distal portion of the inflatable member (1440) may include and/or be formed in an atraumatic shape that reduces trauma to tissue. The catheter shaft (1410) and inflatable member (1440) may be sized for advancement into an endocardial space (e.g., left ventricle). The catheter shaft (1410) may be flexible so as to be deflectable. For example, a deflectable portion of the catheter shaft (1410) may be configured for deflecting a portion of the catheter (1400) including first set of electrodes (1420) and the second set of electrodes (1430, 1432) and the inflatable member (1440) up to about 210 degrees relative to the longitudinal axis. The inflatable member (1440) may be configured to transition between a first configuration (e.g., deflated state) and a second configuration (e.g., inflated state). In the first configuration, the inflatable member (1440) may have a diameter that is about the same as a diameter of the catheter shaft (1410) to aid in advancing the ablation device (1400) through vasculature. For example, the inflatable member (1440) in the first configuration may be approximately parallel to a longitudinal axis of the catheter shaft (1410). The inflatable member (1440) when inflated may bias away from the longitudinal axis.

The first set of electrodes (1420) may be electrically coupled together using one or more electrical leads. The second set of electrodes (1430, 1432) may be electrically coupled together using a different set of electrical leads Accordingly, a bipole may be formed between the first set of electrodes (1420) and the second set of electrodes (1430, 1432) that results in an electric field capable of ablating tissue (e.g., myocardial cells on an inner surface or within a ventricle). For example, the second set of electrodes (1430, 1432) and the first set of electrodes (1420) may each couple to a respective insulated electrical lead, with each lead having sufficient electrical insulation to sustain an electrical potential difference of at least 700 V across its thickness without dielectric breakdown.

The first and second sets of electrodes (1420, 1430, 1432) may include an atraumatic shape to reduce trauma to tissue. For example, the first set of electrodes (1420) may have a set of generally elliptically-shaped electrodes (1420) disposed around a circumference of the inflatable member (1440) In some embodiments, the first set of electrodes (1420) may be located along any portion of the inflatable member (1440) proximal to the second set of electrodes (1430, 1432). The first set of electrodes (1420) may be spaced apart from each other and wired together via one or more insulated leads so as to function as a single electrode (e.g., anode or cathode). The second set of electrodes (1430, 1432) may be disposed on a distal end of the inflatable member (1430, 1432) and electrically isolated from the first set of electrodes (1420).

The first and second set of electrodes (1420, 1430, 1432) may have the same or different sizes, shapes, and/or location along the inflatable member (1440). For example, one or more electrodes of the first and second set of electrodes (1420, 1430, 1432) may have a generally elliptical shape. For example, the second set of electrodes (1430, 1432) may include a distal tip electrode (1430) and a set of generally elliptically-shaped electrodes (1432) disposed around a circumference of the inflatable member (1440). In some embodiments, a longitudinal axis of each of the electrodes (1420, 1432) may be substantially parallel to the longitudinal axis of the catheter shaft (1410) and/or inflatable member (1440). In some embodiments, each electrode of the second set of electrodes (1430, 1432) may be wired together. In other embodiments, subsets of the electrodes of the second set of electrodes (1430, 1432) may be electrically wired together while other subsets (e.g., the distal tip electrode) may be independently addressable. In some embodiments, the distal tip electrode (1432) may be electrically isolated from the first set of electrodes (1420). In some embodiments, one or more electrodes of the first and second set of electrodes (1420, 1430, 1432) may be independently addressable. The distal tip electrode (1430) may be formed at a distal portion of the inflatable member (1440).

In some embodiments, one or more of the electrodes of the first and second sets of electrodes (1420, 1430, 1432) may be configured for receiving or sensing an ECG signal for recording electrophysiology data. The ablation device (1400) may include one or more ECG signal electrodes. For example, one or more electrodes of the second set of electrodes (1430, 1432) may be configured to receive an ECG signal. These ECG signal electrodes, such as the distal tip electrode (1430), may be coupled to its own insulated electrical lead. In these embodiments, the ablation device may be used to record electrophysiology data in place of a mapping catheter before and/or after tissue ablation.

In some embodiments, the first and second set of electrodes (1420, 1430, 1432) may be configured to deliver a pulse waveform from a signal generator to tissue during use. The inflatable member (1440) may be coupled to a distal portion of the catheter shaft (1410) and configured for delivery of irreversible electroporation energy to tissue. The first set of electrodes (1420) and the second set of electrodes (1430, 1432) may have opposite electrical polarities during delivery of a pulse waveform.

The electric field generated by the ablation device (1400) due to conduction between the second set of electrodes (1430, 1432) and the first set of electrodes (1420) through the blood pool and through tissue may result in focal ablation of tissue via irreversible electroporation. The inflatable member (1440) when inflated may have an asymmetric shape in a proximal-to-distal direction, so that one end (for example the distal end) of the inflatable member (1440) is more bulbous than the other end (for example the proximal end) of the inflatable member (1440). The inflatable member (1440) when inflated may be rotationally symmetric about the longitudinal axis of the catheter shaft (1410). In this configuration, the inflatable member (1440) may be placed at an endocardial surface and used to form a lesion via focal ablation (e.g., a spot lesion). The electrode leads may be configured with sufficient insulation and high dielectric strength to be suitable for delivery of irreversible electroporation energy as described herein.

In some embodiments, the catheter shaft (1410) may include a deflectable portion such as in a distal portion of the catheter shaft (1410). The deflectable portion may be configured to deflect up to about 210 degrees relative to the longitudinal axis of the catheter shaft (1410). In some embodiments, an actuator (e.g., fluid source) may be coupled to the inflatable member and configured to transition the inflatable member between the first configuration (e.g., deflated state) and the second configuration (e.g., inflated state) by, for example, using pressurized saline.

Figure 15:
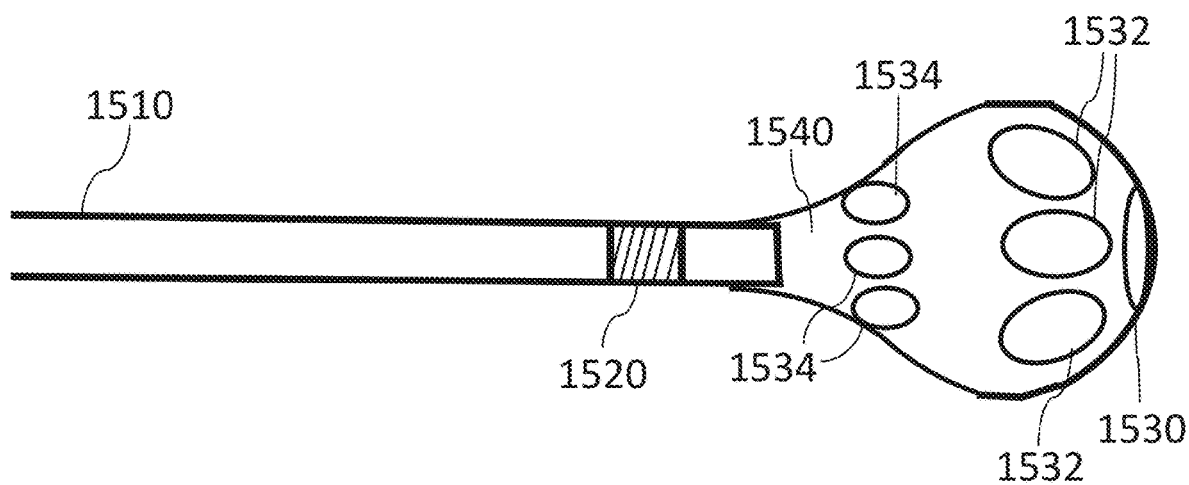
FIG. 15 is a side view of an ablation device, according to other embodiments.

FIG. 15 is a side view of another embodiment of an ablation device (1500) (e.g., structurally and/or functionally similar to the ablation device (110, 200, 300, 500, 500', 500", 500'", 1100, 1200, 1300, 1400) including a catheter shaft (1510) having a first set of electrodes (1520) provided proximal to a second set of electrodes (1530, 1532, 1534) and an inflatable member (e.g., balloon) (1540). The first set of electrodes (1510) may be formed on a surface of a distal portion of the catheter shaft (1510). That is, the first set of electrodes (1520) may be formed on a surface of the distal end of the catheter shaft (1510). The second set of electrodes (1530, 1532, 1534) may be formed on a surface of the inflatable member (1540) and may be electrically isolated from the first set of electrodes (1520). In some embodiments, a major axis (e.g., longitudinal axis) of the second electrodes (1532, 1534) may be substantially parallel to the longitudinal axis of the catheter shaft (1510) and/or inflatable member (1540).

In some embodiments, the ablation device (1500) is useful for forming lesions on endocardial surfaces via focal ablation, such as an inner surface of a ventricle. During use, the electrodes (1520, 1530, 1532, 1534) may be disposed in a ventricle in order to deliver a pulse waveform to ablate tissue, as described in more detail herein. A distal portion of the inflatable member (1540) may include and/or be formed in an atraumatic shape that reduces trauma to tissue. The catheter shaft (1510) and inflatable member (1540) may be sized for advancement into an endocardial space (e.g., left ventricle). The catheter shaft (1510) may be flexible so as to be deflectable. For example, a deflectable portion of the catheter shaft (1510) may be configured for deflecting a portion of the catheter (1500) including the second set of electrodes (1530, 1532, 1534) and the inflatable member (1540) up to about 210 degrees relative to the longitudinal axis. The inflatable member (1540) may be configured to transition between a first configuration (e.g., deflated state) and a second configuration (e.g., inflated state). In the first configuration, the inflatable member (1540) may have a diameter that is about the same as a diameter of the catheter shaft (1510) to aid in advancing the ablation device (1500) through vasculature. For example, the inflatable member (1540) in the first configuration may be approximately parallel to a longitudinal axis of the catheter shaft (1510). The inflatable member (1540) when inflated may bias away from the longitudinal axis. The first set of electrodes (1520) may be structurally and/or functionally similar to the electrodes (220, 230) described with respect to FIGS. 2A-2D.

The first set of electrodes (1520) may be electrically coupled together using one or more electrical leads. The proximal electrodes (1534) of the second set of electrodes and the distal electrodes (1532, 1530) of the second set of electrodes may be electrically wired respectively separately using different sets of electrical leads. In some embodiments, the first set of electrodes (1520) may be configured as an anode while the second set of electrodes (1530, 1532, 1534) may be configured as a cathode, or vice versa. In alternate embodiments, the first set of electrodes (1520) and the proximal electrodes (1534) of the second set of electrodes may be configured as an anode while the distal electrodes (1532, 1530) of the second set of electrodes may be configured as a cathode, or vice versa. For example, the proximal electrodes (1534) of the second set of electrodes, the distal electrodes (1532, 1530) of the second set of electrodes, and the first set of electrodes (1520) may each couple to respective insulated electrical leads, with each lead having sufficient electrical insulation to sustain an electrical potential difference of at least 700 V across its thickness without dielectric breakdown.

The first and second sets of electrodes (1520, 1530, 1532, 1534) may include an atraumatic shape to reduce trauma to tissue. For example, the first set of electrodes (1520) may be ring electrodes. In some embodiments, the first set of electrodes (1520) may be located along any portion of the catheter shaft (1510) proximal to the second set of electrodes (1530, 1532, 1534). The first set of electrodes (1520) may be spaced apart from each other and wired together via one or more insulated leads so as to function as a single electrode (e.g., anode or cathode) while allowing the catheter shaft (1510) to remain flexible and facilitate deflection. The second set of electrodes (1530, 1532, 1534) may be disposed on a surface of the inflatable member (1540) and/or flush with the surface of the inflatable member (1540). The second set of electrodes (1530, 1532) may have the same or different sizes, shapes, and/or location along the inflatable member (1540).

For example, the second set of electrodes (1530, 1532, 1534) may include a distal tip electrode (1530) and a set of generally elliptically-shaped electrodes (1532, 1534) disposed around a circumference of the inflatable member (1540). In some embodiments, a major axis (e.g., longitudinal axis) of each of the electrodes (1532, 1534) may be substantially parallel to the longitudinal axis of the catheter shaft (1510) and/or inflatable member (1540). In some embodiments, the distal tip electrode (1532) may be electrically isolated from the first set of electrodes (1520). In some embodiments, each electrode of the second set of electrodes (1530, 1532, 1534) may be independently addressable. The distal tip electrode (1530) may be formed at a distal portion of the inflatable member (1540) and electrically isolated from the first set of electrodes (1520).

In some embodiments, a set of the second set of electrodes may be electrically coupled with the first set of electrodes. For example, the first set of electrodes (1520) and the proximal electrodes (1534) of the second set of electrodes may be electrically coupled together using one or more electrical leads. In some embodiments, the proximal electrodes (1534) may be formed proximal to a maximum cross-sectional diameter of the inflatable member (1540) when inflated. That is, a proximal portion of the inflatable member (1540) is proximal to a cross-sectional diameter of the inflatable member (1540) at its largest portion. In this configuration the distal electrodes (1530, 1532) of the second set of electrodes may be configured to contact tissue in the second configuration while the first set of electrodes (1520) and the proximal electrodes (1534) of the second set of electrodes may be configured for non-contact with tissue in the second configuration.

In some embodiments, one or more of the electrodes of the first and second sets of electrodes (1520, 1530, 1532, 1534) may be configured for receiving or sensing an ECG signal for recording electrophysiology data. The ablation device (1500) may include one or more ECG signal electrodes. For example, one or more electrodes of the second set of electrodes (1530, 1532, 1534) may be configured to receive an ECG signal. These ECG signal electrodes, such as the distal tip electrode (1530), may be coupled to its own insulated electrical lead. In these embodiments, the ablation device may be used to record electrophysiology data in place of a mapping catheter before and/or after tissue ablation.

The inflatable member (1540) when inflated may have an asymmetric shape in a proximal-to-distal direction, so that one end (for example the distal end) of the inflatable member (1540) is more bulbous than the other end (for example the proximal end) of the inflatable member (1540). The inflatable member (1540) when inflated may be rotationally symmetric about the longitudinal axis of the catheter shaft (1510). In this configuration, the inflatable member (1540) may be placed at an endocardial surface and used to form a lesion via focal ablation (e.g., a spot lesion). The electrode leads may be configured with sufficient insulation and high dielectric strength to be suitable for delivery of irreversible electroporation energy as described herein.

In some embodiments, the catheter shaft (1510) may include a deflectable portion between the first set of electrodes (1520) and the second set of electrodes (1530). In other embodiments the deflectable portion may be proximal to the first set of electrodes (1520). The deflectable portion may be configured to deflect up to about 210 degrees relative to the longitudinal axis of the catheter shaft (1510). In some embodiments, an actuator (e.g., fluid source) may be coupled to the inflatable member and configured to transition the inflatable member between the first configuration (e.g., deflated state) and the second configuration (e.g., inflated state) by, for example, using pressurized saline.

In the embodiments described herein with respect to FIGS. 11-15, the first set of electrodes may be spaced apart from the second set of electrodes by between about 2 mm and about 10 mm. In some embodiments, the first set of electrodes may be formed on a portion of the catheter shaft having a length of between about 2 mm and about 12 mm. In some embodiments, the inflatable member when inflated may have a shape with an effective cross-sectional diameter at its largest portion of between about 5 mm and about 15 mm. In some embodiments, the inflatable member may have a length of up to about 22 mm. For example, the inflatable member may have substantially the same length in the first configuration and the second configuration. In some embodiments, one or more electrodes of the first set of electrodes may have a width of between about 1 mm and about 5 mm and may be spaced apart by between about 1 mm and about 5 mm. In some embodiments, a distal-most electrode of the first set of electrodes may be spaced apart by at least about 5 mm from a proximal end of the inflatable member when inflated.

II. Methods

Also described here are methods for ablating tissue in a heart chamber using the systems and devices described above. The heart chamber may include one or more of the right, left ventricle, and/or right, left atria. Generally, the methods described here include introducing and disposing a device in contact with one or more chambers such as the ventricles. A pulse waveform may be delivered by one or more electrodes and an inflatable member (e.g., balloon) of the device to ablate tissue. In some embodiments, a cardiac pacing signal may synchronize the delivered pulse waveforms with the cardiac cycle. Additionally or alternatively, the pulse waveforms may include a plurality of levels of a hierarchy to reduce total energy delivery. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate.

In some embodiments, the ablation devices described herein may be used for focal ablation of cardiac features/structures identified to cause arrhythmia. For example, a cardiac electrophysiology diagnostic catheter (e.g., mapping catheter) may be used to map cardiac structures such as re-entrant circuits and ventricular scar tissue that may be subsequently ablated through focal ablation using any of the ablation devices described herein. Focal ablation may, for example, create a spot lesion that neutralizes a re-entrant circuit while sparing surrounding tissue. In some embodiments, one or more focal ablation lesions may be formed in combination with one or more box or line lesions to treat cardiac arrhythmia. As a non-limiting example, in some embodiments, a system can include one or more mapping catheters, one or more ablation devices (e.g., as illustrated in FIGS. 2A-2C and 3) useful for creating lesions via focal ablation.

Figure 4A:
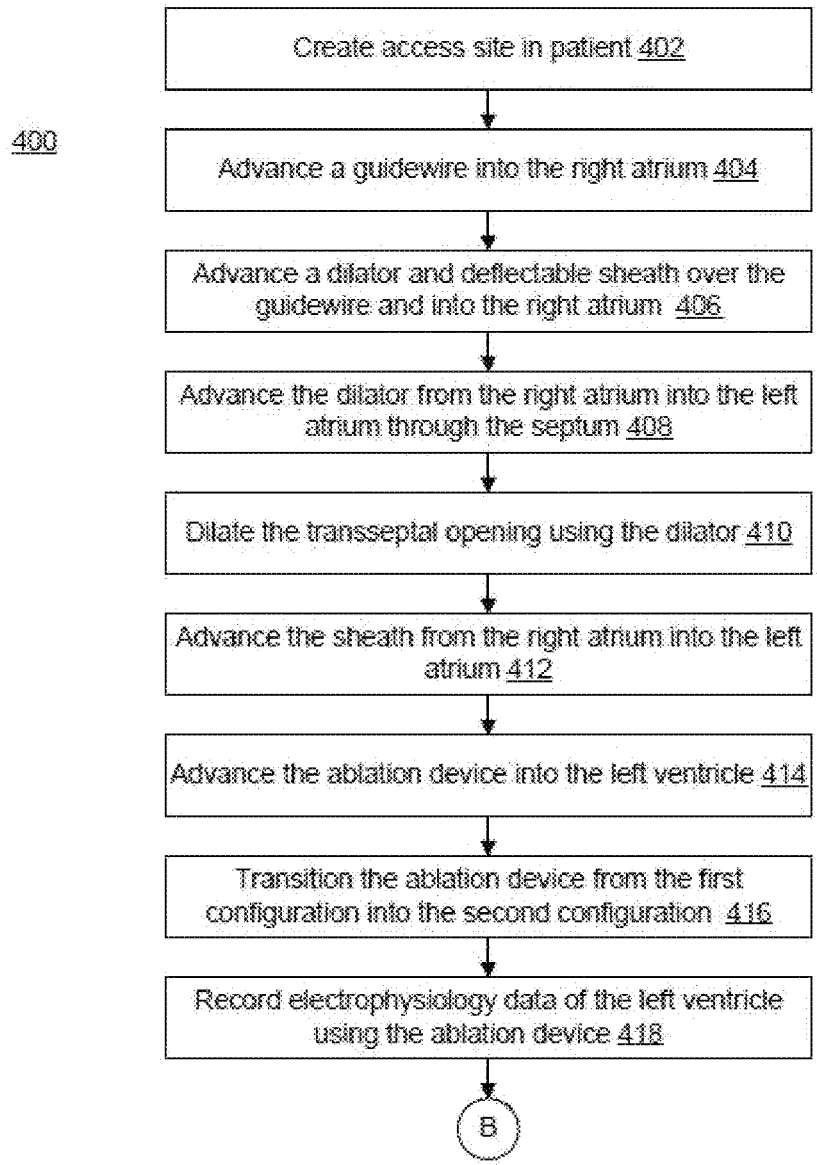
FIGS. 4A-4B illustrates a method for tissue ablation, according to embodiments.
Figure 4B:
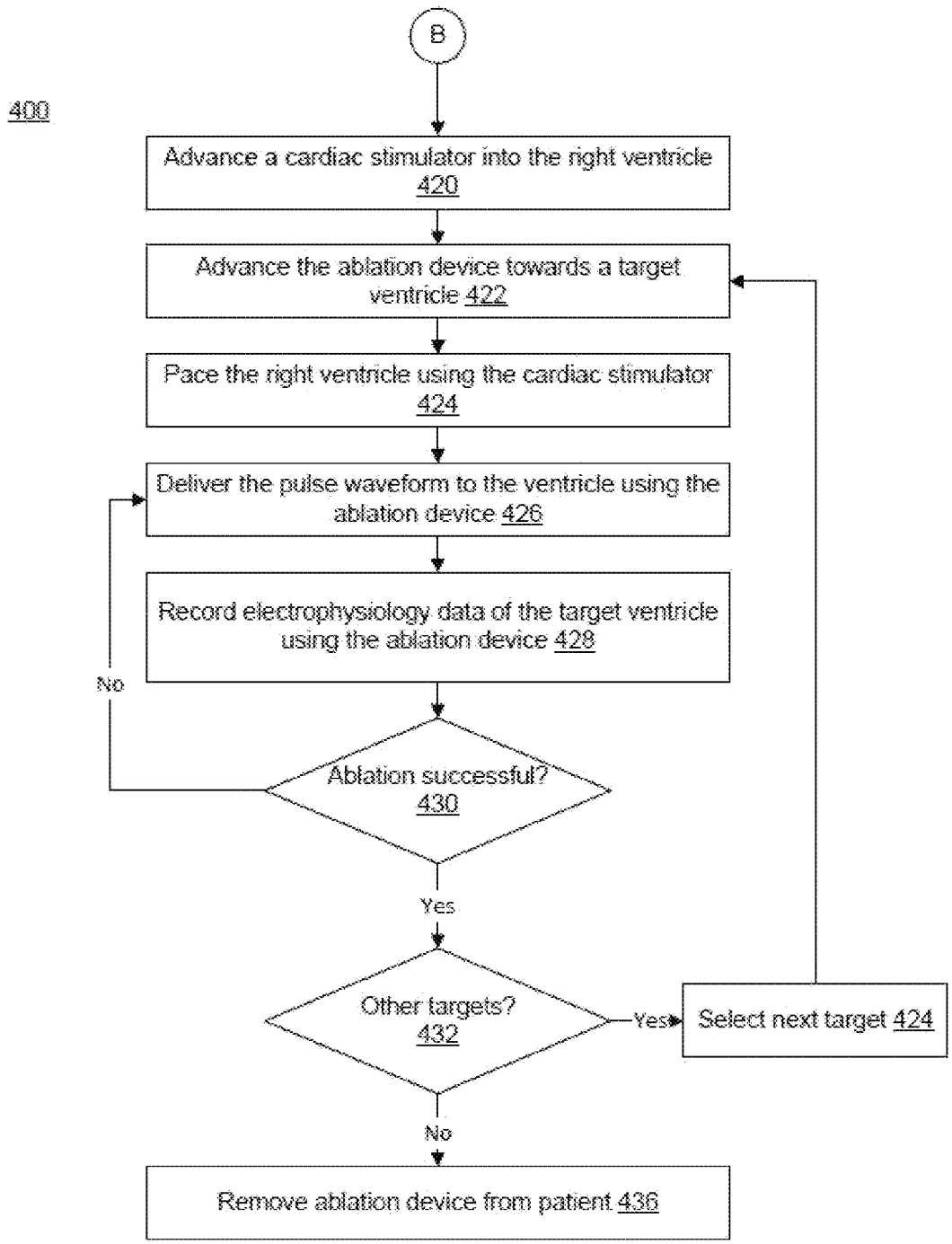

Generally, and as illustrated in FIGS. 4A-4B, a method (400) includes the introduction of a device (e.g., ablation device, such as the ablation devices (110, 200, 300, 500, 500', 500'', 500''', 1100, 1200, 1300, 1400, 1500) into an endocardial space of a ventricle. The ablation device may be introduced in a first configuration and transitioned to a second configuration in the ventricle. Once positioned in the ventricle, voltage pulse waveforms may be applied to tissue during a refractory period of the cardiac cycle. Electrophysiology data of the ventricle may be recorded to determine efficacy of the ablation.

The method (400) may begin with creating an access site in a patient (402). For example, to access the left ventricle for treatment, an antegrade delivery approach may be used, in which the first access site may be via a femoral vein of the patient. A guidewire may be advanced into the access site via the femoral vein and into the right atrium of the patient (404). A dilator and a deflectable sheath may be advanced over the guidewire and into the right atrium (406). The sheath may, for example, be configured for deflecting up to about 210 degrees. The dilator may be advanced from the right atrium into the left atrium through the septum (408) to create a transseptal opening. For example, the dilator may be advanced from the right atrium into the left atrium through the interatrial septum to create the transseptal opening. The interatrial septum may include the fossa ovalis of the patient. The transseptal opening may be dilated using the dilator (410). For example, the dilator may be advanced out of the sheath and used to poke the fossa ovalis to create the transseptal opening (assuming the patient is heparinized). Alternatively, a transseptal needle (e.g., Brockenbrough needle) may be used to create the transseptal opening. The sheath may be advanced from the right atrium into the left atrium (412) through the transseptal opening. An ablation device may be advanced into the left ventricle over the guidewire (414) via the mitral valve. Alternatively, the left ventricle may be accessed by a retrograde approach, in which the first access site may be via a femoral artery of the patient, and a guidewire and ablation device may be advanced through an aorta of the patient, and then through the aortic valve into the left ventricle. For treatment of the right ventricle, the first access site may again be via a femoral vein of the patient, and the guidewire and ablation device may be advanced into the right atrium of the patient and then through the tricuspid valve into the right ventricle.

In some embodiments, the ablation device may include a catheter shaft lumen and a set of insulated electrical leads extending through the shaft lumen. The catheter shaft may include one or more electrodes formed on a surface of the shaft. In some embodiments, one or more electrodes may be disposed on one or more portions of the inflatable member. For example, an electrode may be disposed on a distal end of the inflatable member. One or more of the electrodes may be configured to receive electrophysiology signals from the ventricle. In the method of FIGS. 4A-4B, an ablation device may be configured to record electrophysiology data of the ventricle. In some embodiments, to allow the ablation device to record electrophysiology data, the ablation device may be transitioned from the first configuration into the second configuration (416) within the ventricle (e.g., left ventricle). In some embodiments, the inflatable member may be transitioned between the first and second configurations using a handle of the ablation device. For example, the handle may include a saline flow control mechanism to control a volume of saline within an inflatable member. The handle may further include a saline volume indicator to indicate a configuration of the inflatable member. The ablation device in the second configuration may be configured to record electrophysiology data using the ablation device (418). For example, one or more electrodes on the catheter shaft and inflatable member may be configured for receiving an ECG signal for recording electrophysiology data.

In other embodiments, a separate diagnostic device (e.g., a mapping catheter) may be used to record electrophysiology data of the ventricle to be treated. Electrophysiology data may be used to generate an anatomical map that may be used to compare electrophysiology data recorded after energy delivery (e.g., ablation). The diagnostic device may be advanced into the selected ventricle via a femoral vein or jugular vein. In these embodiments, the diagnostic device (e.g., second catheter) may be advanced into the right ventricle (via the tricuspid valve) or into the ventricle (via the left atrium and the mitral valve) over the guidewire after step (412) instead of advancing the ablation device into the selected ventricle. The second catheter may be used to record electrophysiology data of one or more ventricles. Once completed, the diagnostic device may be withdrawn from the body over the guidewire, and the ablation device may then be advanced over the guidewire into the selected ventricle.

Still referring to FIGS. 4A-4B, a second access site may be created in the patient to advance a lead or catheter for cardiac stimulation into the patient's heart. For example, the second access site may be via a jugular vein of the patient. The device for cardiac stimulation may be advanced into the right ventricle through the second access site (420) (e.g., near the apex of the right ventricle). A pacing signal may be generated by a cardiac stimulator and applied to the heart for cardiac stimulation of the heart. An indication of the pacing signal may be transmitted from the cardiac stimulator to the signal generator. In some embodiments, the operator may confirm the pacing capture and determine that the ventricle is responding to the pacing signal as intended. For example, pacing capture may be confirmed on an ECG display on a signal generator. Confirmation of pacing capture is a safety feature in that ablation is delivered in synchrony with pacing through enforced periodicity of a Q-wave through pacing.

The ablation device may be advanced towards a target ventricle (422) for delivering a pulse waveform configured for tissue ablation. In particular, the ablation device in the second configuration may be advanced towards a ventricle of the heart to contact a tissue surface. The sheath may be deflected as needed to direct the ablation device towards the target ventricle. The inflatable member may be transitioned to a second configuration where the inflatable member inflates to contact the inflatable member against the ventricle at a predetermined location. Once the ablation device is in position within the heart to deliver one or more pulse waveforms, an extension cable may be used to electrically couple a signal generator to a proximal end of the handle of the ablation device. After pacing the right ventricle using the pacing device (424), the pulse waveform may be delivered to the ventricle using the ablation device to ablate tissue in a portion of the target ventricle (426). The pulse waveform may be delivered in synchronization with the pacing signal.

As described in detail in the figures (e.g., FIGS. 5A-5J), the ablation device may be configured to generate an electric field intensity in a region of myocardial tissue of a ventricle (e.g., where there may be re-entrant circuits, etc.) that is large enough to cause irreversible electroporation in tissue. For example, the inflatable member of the ablation device in FIG. 5D may be in contact with a tissue surface and may be used to generate a set of high intensity electric field lines that penetrate the ventricle at a depth of between about 5 mm to about 8 mm or more to form one or more focal ablation lesions, as shown by the spatial zone (532) in FIG. 5E. The ablation zone corresponding to the spatial region (532) may be wide and deep. The size of the inflatable member may be modified to control a depth and strength of the electric field.

This allows energy to be delivered more efficiently and thus permits tissue ablation with minimal total energy delivered.

While examples of ablation devices configured for delivery of irreversible electroporation pulsed electric field therapy have been described here, the examples described herein are provided for exemplary purposes only and those skilled in the art may devise other variations without departing from the scope of the present invention. For example, a range and variety of materials, polyhedral sides, electrode diameters, device dimensions, voltage levels, proximal electrodes, and other such details are possible and may be implemented as convenient for the application at hand without departing from the scope of the present invention. The catheter shaft may undergo a range of deflections by controlling deflection from a catheter handle. The metallized electrode portions disposed on the inflatable member embodiments may be used for ECG signal recording or irreversible electroporation therapy delivery or both.

As discussed herein, the pulse waveform may be generated by a signal generator coupled to the ablation device. The signal generator may be electrically coupled to a proximal end of a handle of the ablation device. For example, an extension cable may electrically couple the signal generator to the proximal end of the handle. In some embodiments, the pulse waveform may include a time offset with respect to the pacing signal. In some embodiments, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval. A fourth level of the hierarchy of the pulse waveform may include a plurality of third sets of pulses as a fourth set of pulses. A fourth time interval may separate successive third sets of pulses. The fourth time interval may be at least ten times the duration of the third level time interval.

One or more electrodes of the ablation device in the second configuration may be configured to receive electrophysiology signals of the target ventricle and used to record electrophysiology data of the target ventricle (428). The electrophysiology data may be compared to the baseline data recorded prior to ablation to determine if ablation was successful (430).

In other embodiments, the ablation device may be withdrawn from the heart over the guidewire and a mapping catheter may be advanced over the guidewire to record the post-ablation electrophysiology data of the target ventricle. If the ablation is not successful (430—NO) based on the electrophysiology data and predetermined criteria, then the process may return to step 426 for delivery of additional pulse waveforms. The pulse waveform parameters may be the same or changed for subsequent ablation cycles.

If analysis of the electrophysiology data indicates that the ablation of a ventricle portion is successful (e.g., tissue portion is electrically silent) (430—YES), then a determination may be made of other target ventricle portions to ablate (432). Another target ventricle portion may be selected (424) and the process may return to step 422 when other ventricular portions are to be ablated. When switching between target ventricles, the inflatable member may be at least partially deflated, and the ablation device may be advanced towards another portion of tissue. If no other portions are to be ablated (432—NO), the ablation device, cardiac stimulator, sheath, guidewire, and the like, may be removed from the patient (436).

In other embodiments, the diagnostic device (e.g., mapping catheter) may be used to record electrophysiology data of the ventricle after pulse waveforms are delivered to tissue by the ablation device. In these embodiments, the ablation device may be withdrawn from the patient over the guidewire after steps 426 or 436 and the diagnostic device may be advanced into the ventricle over the guidewire to record electrophysiology data of the target ventricle having undergone tissue ablation.

It should be noted that for any of the steps described herein, a radiopaque portion of the ablation device may be fluoroscopically imaged to aid an operator. For example, visual confirmation may be performed through fluoroscopic imaging that the inflatable members in the second configuration is in contact with the ventricle or to visually confirm an apposition of the inflatable member and electrodes relative to the ventricle. Imaging from a plurality of angles may be used to confirm positioning.

It should be understood that the examples and illustrations in this disclosure serve exemplary purposes and departures and variations such as inflatable member characteristics, number of electrodes, and so on can be built and deployed according to the teachings herein without departing from the scope of this invention.

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (100), devices (e.g., 200, 300), and methods (e.g., 400) described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be sequentially triggered based on a pre-determined sequence, and in one embodiment the sequenced delivery can be triggered from a cardiac stimulator and/or pacing device. In some embodiments, the ablation pulse waveforms are applied in a refractory period of the cardiac cycle so as to avoid disruption of the sinus rhythm of the heart. One example method of enforcing this is to electrically pace the heart with a cardiac stimulator and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities involving the frequency of cardiac pacing.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn can broaden the areas of clinical application of electroporation including therapeutic treatment of a variety of cardiac arrhythmias.

Figure 6:
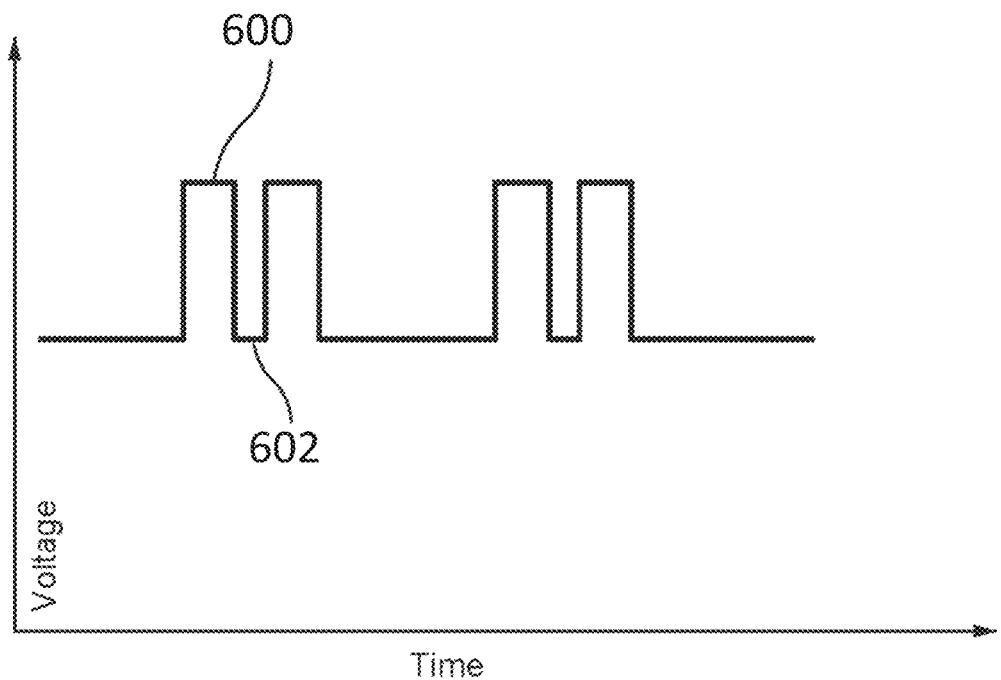
FIG. 6 is an example waveform showing a sequence of voltage pulses with a pulse width defined for each pulse, according to embodiments.

FIG. 6 illustrates a pulsed voltage waveform in the form of a sequence of rectangular double pulses, with each pulse, such as the pulse (600) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 6 illustrates a set of monophasic pulses where the polarities of all the pulses are the same (all positive in FIG. 6, as measured from a zero baseline). In some embodiments, such as for irreversible electroporation applications, the height of each pulse (600) or the voltage amplitude of the pulse (600) can be in the range from about 400 volts, about 1,000 volts, about 5,000 volts, about 10,000 volts, about 15,000 volts, including all values and sub ranges in between. As illustrated in FIG. 6, the pulse (600) is separated from a neighboring pulse by a time interval (602), also sometimes referred to as a first time interval. The first time interval can be about 3 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 7:
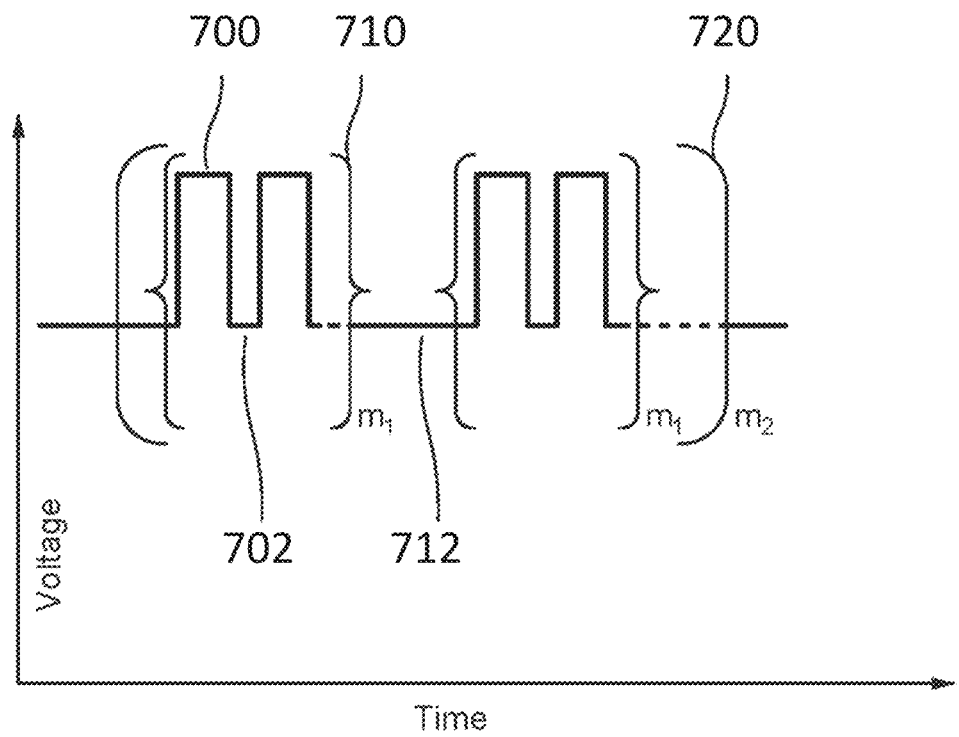
FIG. 7 schematically illustrates a hierarchy of pulses showing pulse widths, intervals between pulses, and groupings of pulses, according to embodiments.

FIG. 7 introduces a pulse waveform with the structure of a hierarchy of nested pulses. FIG. 7 shows a series of monophasic pulses such as pulse (700) with pulse width/pulse time duration w, separated by a time interval (also sometimes referred to as a first time interval) such as (702) of duration $t_1$ between successive pulses, a number $m_1$ of which are arranged to form a group of pulses (710) (also sometimes referred to as a first set of pulses). Furthermore, the waveform has a number $m_2$ of such groups of pulses (also sometimes referred to as a second set of pulses) separated by a time interval (712) (also sometimes referred to as a second time interval) of duration $t_2$ between successive groups. The collection of $m_2$ such pulse groups, marked by (720) in FIG. 7, constitutes the next level of the hierarchy, which can be referred to as a packet and/or as a third set of pulses. The pulse width and the time interval $t_1$ between pulses can both be in the range of microseconds to hundreds of microseconds, including all values and sub ranges in between. In some embodiments, the time interval $t_2$ can be at least three times larger than the time interval $t_1$. In some embodiments, the ratio $t_2/t_1$ can be in the range between about 3 and about 300, including all values and sub-ranges in between.

Figure 8:
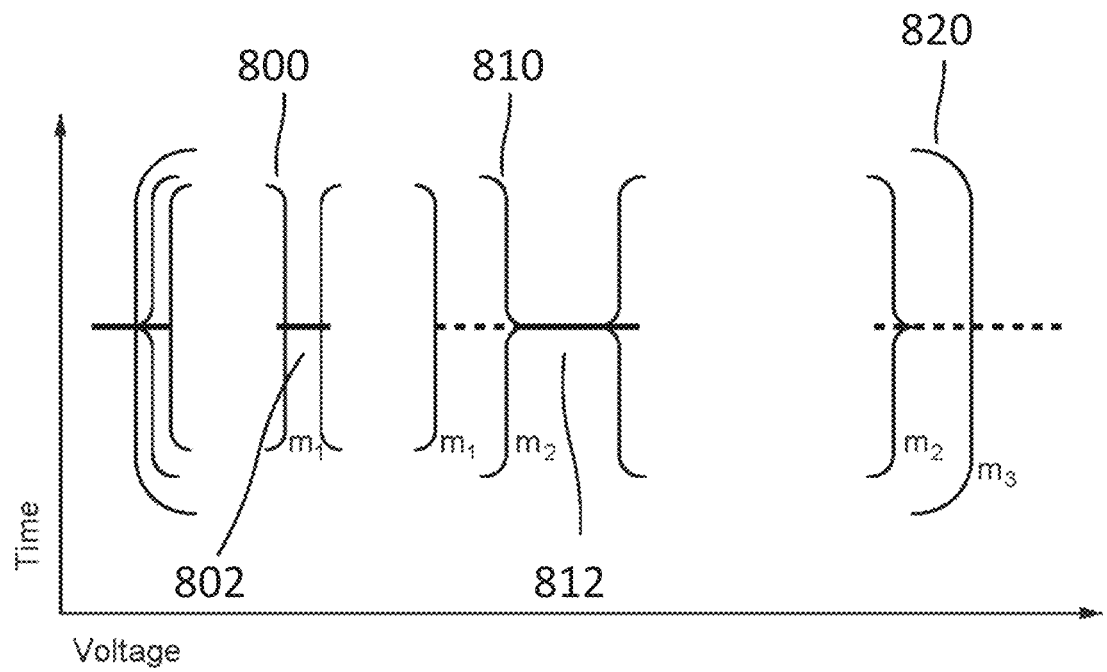
FIG. 8 provides a schematic illustration of a nested hierarchy of monophasic pulses displaying different levels of nested hierarchy, according to embodiments.

FIG. 8 further elaborates the structure of a nested pulse hierarchy waveform. In this figure, a series of $m_1$ pulses (individual pulses not shown) form a group of pulses (800) (e.g., a first set of pulses). A series of $m_2$ such groups separated by an inter-group time interval (810) of duration $t_2$ (e.g., a second time interval) between one group and the next form a packet (e.g., a second set of pulses). A series of $m_3$ such packets separated by time intervals (812) of duration $t_3$ (e.g., a third time interval) between one packet and the next form the next level in the hierarchy, a super-packet labeled (820) (e.g., a third set of pulses) in the figure. In some embodiments, the time interval $t_3$ can be at least about thirty times larger than the time interval $t_2$. In some embodiments, the time interval $t_3$ can be at least fifty times larger than the time interval $t_2$. In some embodiments, the ratio $t_3/t_2$ can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 9:
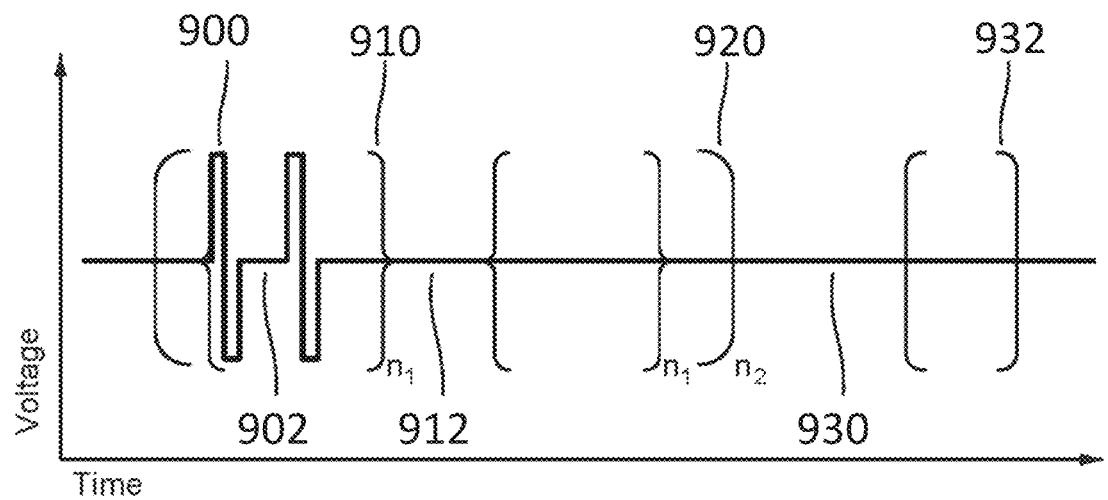
FIG. 9 is a schematic illustration of a nested hierarchy of biphasic pulses displaying different levels of nested hierarchy, according to embodiments.

FIG. 9 provides an example of a biphasic waveform sequence with a hierarchical structure. In the example shown in the figure, biphasic pulses such as (900) have a positive voltage portion as well as a negative voltage portion to complete one cycle of the pulse. There is a time delay (902) (e.g., a first time interval) between adjacent cycles of duration $t_1$, and $n_1$ such cycles form a group of pulses (910) (e.g., a first set of pulses). A series of $n_2$ such groups separated by an inter-group time interval (912) (e.g., a second time interval) of duration $t_2$ between one group and the next form a packet (920) (e.g., a second set of pulses). The figure also shows a second packet (930), with a time delay (932) (e.g., a third time interval) of duration $t_3$ between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays $t_1$ can be in the range from zero to several microseconds. The inter-group time interval $t_2$ can be at least ten times larger than the pulse width. In some embodiments, the time interval $t_3$ can be at least about twenty times larger than the time interval $t_2$. In some embodiments, the time interval $t_3$ can be at least fifty times larger than the time interval $t_2$.

Embodiments disclosed herein include waveforms structured as hierarchical waveforms that include waveform elements/pulses at various levels of the hierarchy. The individual pulses such as (700) in FIG. 7 comprise the first level of the hierarchy, and have an associated pulse time duration and a first time interval between successive pulses. A set of pulses, or elements of the first level structure, form a second level of the hierarchy such as the group of pulses/second set of pulses (710) in FIG. 7. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (720) in FIG. 7. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 200 milliseconds, including all values and sub ranges in between. The generally iterative or nested structure of the waveforms can continue to a higher plurality of levels, such as ten levels of structure, or more.

For example, a pulse waveform may include a fourth level of the hierarchy of the pulse waveform may include a plurality of third sets of pulses as a fourth set of pulses, a fourth time interval separating successive third sets of pulses, the fourth time interval being at least ten times the duration of the third level time interval.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

Figure 10:
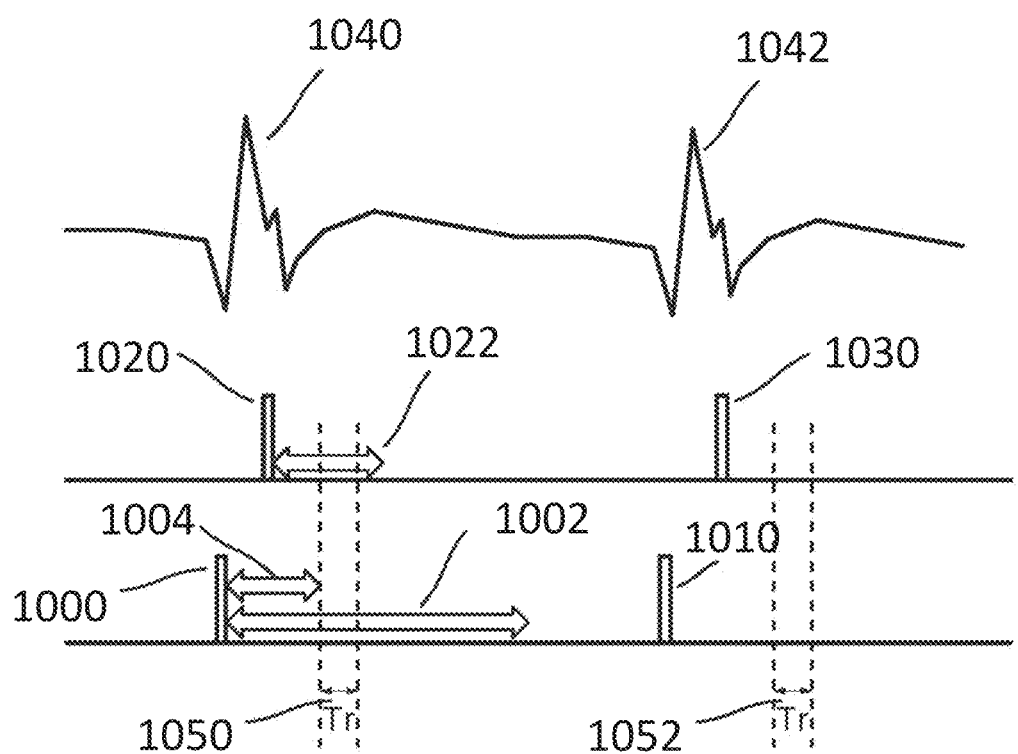
FIG. 10 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein are applied during the refractory period of the cardiac cycle so as to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms can be delivered. FIG. 10 illustrates an example where both atrial and ventricular pacing is applied (for instance, with pacing leads or catheters situated in the right atrium and right ventricle respectively). With time represented on the horizontal axis, FIG. 10 illustrates a series of ventricular pacing signals such as (1000) and (1010), and a series of atrial pacing signals (1020, 1030), along with a series of ECG waveforms (1040, 1042) that are driven by the pacing signals. As indicated in FIG. 10 by the thick arrows, there is an atrial refractory time window (1022) and a ventricular refractory time window (1002) that respectively follow the atrial pacing signal (1022) and the ventricular pacing signal (1000). As shown in FIG. 10, a common refractory time window (1050) of duration $T_r$ can be defined that lies within both atrial and ventricular refractory time windows (1022, 1002). In some embodiments, the electroporation ablation waveform(s) can be applied in this common refractory time window (1050). The start of this refractory time window (1022) is offset from the pacing signal (1000) by a time offset (1004) as indicated in FIG. 10. The time offset (1004) can be smaller than about 25 milliseconds, in some embodiments. At the next heartbeat, a similarly defined common refractory time window (1052) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy can be applied over a heartbeat, so that a series of packets is applied over a series of heartbeats, for a given electrode set.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. An apparatus for delivering a pulse waveform to tissue, the apparatus comprising:
   a catheter shaft defining a longitudinal axis and having a catheter distal end;
   an inflatable member including a proximal end and a distal end opposite to the proximal end, the inflatable member having an asymmetric shape in a proximal-to-distal direction, the distal end being more bulbous than the proximal end, the proximal end of the inflatable member being adjacent to and coupled to the catheter distal end and the distal end of the inflatable member being spaced apart from and not coupled to the catheter distal end;

a first set of electrodes formed on a surface of the catheter shaft; and a second set of electrodes formed on the inflatable member at a location distal to the catheter distal end and electrically isolated from the first set of electrodes, the second set of electrodes including a tip electrode formed on a surface at the distal end of the inflatable member;

wherein the catheter shaft includes a deflectable portion formed between the first set of electrodes and the second set of electrodes, the deflectable portion configured for deflecting a portion of the catheter including the second set of electrodes and the inflatable member up to about 210 degrees relative to the longitudinal axis.

2. The apparatus of claim 1, wherein the second set of electrodes are formed on the inflatable member on an approximate plane approximately perpendicular to the longitudinal axis.

3. The apparatus of claim 1, wherein each electrode of the second set of electrodes has a circular or elliptical shape.

4. The apparatus of claim 3, wherein a major axis of each electrode of the second set of electrodes having the elliptical shape is substantially parallel to the longitudinal axis.

5. The apparatus of claim 1, the first set of electrodes having a polarity opposite to a polarity of the second electrode during delivery of a pulse waveform.

6. The apparatus of claim 1, wherein one or more electrodes of the first set of electrodes and one or more electrodes of the second electrode has an insulated electrical lead associated therewith, the insulated electrical lead configured for sustaining a voltage potential of at least about 700 V without dielectric breakdown of its corresponding insulation, the insulated electrical lead disposed in a lumen of the catheter shaft.

7. The apparatus of claim 1, wherein a distal-most electrode of the first set of electrodes is spaced apart from a proximal most electrode of the second set of electrodes by between about 4 mm and about 10 mm.

8. The apparatus of claim 1, wherein a distal-most electrode of the first set of electrodes is spaced apart by at least about 5 mm from a proximal end of the inflatable member.

9. The apparatus of claim 1, wherein the first set of electrodes are formed on a portion of the catheter shaft having a length of between about 3 mm and about 12 mm.

10. The apparatus as in claim 1, further including a conductive element formed on a surface of the inflatable member, the conductive element being electrically connected to the second set of electrodes.

11. The apparatus of claim 10, wherein the conductive element includes a set of spaced apart conductive stripes extending between ends of the inflatable member, wherein the set of spaced apart conductive stripes intersect each other at the proximal and distal ends of the inflatable member.

12. The apparatus of claim 1, further including a first conductive element disposed on an outer surface of the inflatable member and a second conductive element disposed on an inner surface of the inflatable member, wherein the first conductive element has an opposite polarity to the second conductive element during delivery of a pulse waveform.

13. The apparatus as in claim 1, wherein a distal end of the inflatable member has a concave surface facing away from a proximal end of the inflatable member, wherein the second electrode is formed on the concave surface.

14. The apparatus of claim 1, wherein each electrode of the second set of electrodes has a diameter of between about 3 mm and about 15 mm.

15. The apparatus of claim 1, wherein the inflatable member is transitionable between a first configuration and a second configuration, the inflatable member in the second configuration having a cross-sectional diameter at its largest portion of between about 6 mm and about 22 mm.

16. The apparatus of claim 1, wherein the second set of electrodes is formed on a distal portion of the inflatable member located distal to an equatorial plane of the inflatable member, the apparatus further comprising a third set of electrodes formed on the inflatable member at a location proximal to the equatorial plane of the inflatable member.

17. An apparatus for delivering a pulse waveform to tissue, the apparatus comprising:

a catheter shaft defining a longitudinal axis and having a catheter distal end;

an inflatable member including a proximal end and a distal end opposite to the proximal end, the proximal end of the inflatable member being adjacent to and coupled to the catheter distal end and the distal end of the inflatable member being spaced apart from and not coupled to the catheter distal end;

a first set of electrodes formed on an outer surface of the catheter shaft; and a second set of electrodes formed on an inner surface of the catheter shaft and the inflatable member at a location distal to the catheter distal end and electrically isolated from the first set of electrodes, the second set of electrodes including a distal electrode formed on the inner surface of the catheter shaft and a tip electrode formed on an outer surface at the distal end of the inflatable member, and an electrical lead coupling the distal electrode and the tip electrode.

18. An apparatus for delivering a pulse waveform to tissue, the apparatus comprising:

a catheter shaft defining a longitudinal axis and having a catheter distal end;

an inflatable member including a proximal end and a distal end opposite to the proximal end, the inflatable member having a polyhedron shape including a plurality of faces, the proximal end of the inflatable member being adjacent to and coupled to the catheter distal end and the distal end of the inflatable member being spaced apart from and not coupled to the catheter distal end;

a first set of electrodes formed on a surface of the catheter shaft; and a second set of electrodes formed on the plurality of faces of the inflatable member at a location distal to the catheter distal end and electrically isolated from the first set of electrodes, the second set of electrodes including a tip electrode formed on a surface at the distal end of the inflatable member.

19. The apparatus of claim 18, wherein one or more of the second set of electrodes includes a concave curved shape such that a pocket is formed.

20. The apparatus of claim 18, wherein each of the plurality of faces include edges having a stiffness higher than a surface of the face such that the plurality of faces are indented.

* * * * *